United States Patent
Blum

(10) Patent No.: US 10,072,289 B2
(45) Date of Patent: Sep. 11, 2018

(54) GENETIC ADDICTION RISK ANALYSIS FOR RDS SEVERITY INDEX

(71) Applicant: SYNAPTAMINE, INC., Austin, TX (US)

(72) Inventor: Kenneth Blum, Austin, TX (US)

(73) Assignee: IGENE LLC, Austin, TX (US)

( * ) Notice: Subject to any disclaimer, the term of this patent is extended or adjusted under 35 U.S.C. 154(b) by 0 days.

(21) Appl. No.: 14/796,989

(22) Filed: Jul. 10, 2015

(65) Prior Publication Data

US 2016/0012180 A1 Jan. 14, 2016

Related U.S. Application Data

(60) Provisional application No. 62/023,144, filed on Jul. 10, 2014.

(51) Int. Cl.
| | | |
|---|---|---|
| *G06F 19/00* | (2018.01) | |
| *C12Q 1/6827* | (2018.01) | |
| *G16H 50/30* | (2018.01) | |
| *C12Q 1/6883* | (2018.01) | |
| *G06F 19/20* | (2011.01) | |
| *G06F 19/22* | (2011.01) | |
| *G06F 19/24* | (2011.01) | |
| *G06F 19/18* | (2011.01) | |

(52) U.S. Cl.
CPC ......... *C12Q 1/6827* (2013.01); *C12Q 1/6883* (2013.01); *G06F 19/00* (2013.01); *G06F 19/18* (2013.01); *G06F 19/20* (2013.01); *G06F 19/22* (2013.01); *G06F 19/24* (2013.01); *G16H 50/30* (2018.01); *C12Q 2537/165* (2013.01); *C12Q 2600/124* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 6,538,120 B1 | 3/2003 | Hoehe et al. | |
| 2006/0062859 A1* | 3/2006 | Blum | A61K 31/56 424/725 |
| 2011/0189161 A1 | 8/2011 | Blum et al. | |
| 2011/0294680 A1 | 12/2011 | Rose et al. | |
| 2012/0053070 A1* | 3/2012 | Blum | C12Q 1/6883 506/9 |

OTHER PUBLICATIONS

Al-Eitan et al. "Custom genotyping for substance addiction susceptibility genes in Jordanians of Arab descent," BMC Research Notes, Sep. 10, 2012 (Sep. 10, 2012), vol. 5, pp. 1-11.
Blum et al. "Genetic Addiction Risk Score (GARS) analysis: Exploratory development of polymorphic risk alleles in polydrug addicted males," Int. J. Omics Biotechnol. Jul. 8, 2010 (Jul. 8, 2010), pp. 169-175.

* cited by examiner

*Primary Examiner* — Jason M Sims
(74) *Attorney, Agent, or Firm* — Dickinson Wright PLLC; Ross Spencer Garsson

(57) ABSTRACT

Methods and kits for assessing severity index for alcohol abuse, drug abuse, and other reward deficiency syndromes. It has been discovered that a multifaceted non-specific RDS behaviors should be considered as the true "reward" phenotype (endophenotype) instead of a single subset RDS behavior such as alcoholism. In an embodiment of the present invention, it has been discovered that there are at least eleven risk alleles associated with ten candidate genes. The methods and kits of the present invention satisfy the need to classify patients at genetic risk for drug/alcohol seeking behavior prior to or upon entry to residential and or non-residential chemical dependency and pain programs.

22 Claims, No Drawings
Specification includes a Sequence Listing.

GENETIC ADDICTION RISK ANALYSIS FOR RDS SEVERITY INDEX

RELATED PATENT APPLICATIONS

This claims the benefit of provisional U.S. Patent Application Ser. No. 62/023,144, filed on Jul. 10, 2014, entitled "Genetic Addiction Risk Score (GARS$_{RX}$™) Panel Predicts Addiction Severity Index for Alcohol and Drugs." This patent application is commonly assigned to the Assignee of the present invention and is hereby incorporated herein by reference in its entirety for all purposes.

This application is also related to, but does not claim the benefit, of U.S. patent application Ser. No. 13/092,894, filed Apr. 22, 2011, entitled "Genetic Risk Analysis In Reward Deficiency Syndrome," and U.S. patent application Ser. No. 14/247,240, filed Apr. 7, 2014, entitled "Method to Assess Treatment Outcomes in Reward Deficiency Syndrome (RDS) Behaviors Utilizing Expression Profiling." These patent applications are also hereby incorporated by reference in their entirety for all purposes.

TECHNICAL FIELD

This disclosure relates to methods and kits for assessing severity index for alcohol abuse, drug abuse, and other reward deficiency syndromes.

BACKGROUND

In 2013, it was noted in Blum 2013, Chapter 2, Section, 2.5, p. 39:

When almost half-of the US population have indulged in illegal drug practices, when our presidential candidates are forced to dodge the tricky question of their past history involving illegal drug use, and when almost every American has sloshed down a martini or two in their life time, there must be a reason, there must be a need, there must be a natural response for humans to imbibe at such high rates. There is even a more compelling question surrounds the millions who seek out high risk novelty. Why do millions have this innate drive in face of putting themselves in Harm's way? Why are millions paying the price of their indiscretions in our jails, in hospitals, in wheel chairs and are lying dead in our cemeteries. What price must we pay for pleasure seeking or just plain getting "HIGH"? Maybe the answer lies within our brain. Maybe it is in our genome?

Reward Deficiency Syndrome (RDS) was first defined by the inventor and his lab in 1996 as a putative predictor of impulsive and addictive behaviors. [Blum 2000; Blum 1996; Comings 2000]. See also TABLE 1.

TABLE 1

The Reward Deficiency Syndrome Behaviors (RDS).

| ADDITIVE BEHAVIORS | | IMPULSE BEHAVIORS | | OBESSIVE | |
| --- | --- | --- | --- | --- | --- |
| Substance Related | Non Substance Related | Spectrum Disorders | Disruptive Impulsive | COMPULSIVE BEHAVIORS | PERSONALITY DISORDERS |
| Alcohol | Thrill seeking (novelty) | Attention-deficit Hyperactivity | Anti-social | Body Dysmorphic | Paranoid |
| Cannabis | Sexual Sadism | Tourette and Tic Syndrome | Conduct | Hoarding | Schizoid |
| Opioids | Sexual Masochism | Autism | Intermittent Explosive | Trichotillomania (hair pulling) | Borderline |
| Sedatives/ Hypnotics | Hypersexual | | Oppositional Defiant | Excoriation (skin picking) | Schizotypal |
| Stimulants | Gambling | | Exhibitionistic | Non-suicidal Self-Injury | Histrionic |
| Tobacco | Internet Gaming | | | | Narcissistic |
| Glucose | | | | | Avoidant |
| Food | | | | | Dependent |

The molecule dopamine after binding to the dopamine D2 receptor has been associated with many behaviors (Dackis and Gold 1985; Di Chiara and Imperato 1988) and the DRD2 has been referred to as a reward gene [Blum et al 1990; Eisenberg 2007; Hietala I 1994; Hietala II 1994; Volkow 2001; Volkow 2002]. Although the DRD2 gene and especially the TaqI A1 allele have been most associated with neuropsychiatric disorders in general, in alcoholism, and other addiction (carbohydrate) reward behaviors, it may also be involved in co-morbid antisocial personality disorder symptoms (especially in children and adults with attention deficit hyperactivity disorder (ADHD) or Tourette's Syndrome) and high novelty seeking.

Dopamine has been called the "anti-stress molecule" and/or the "pleasure molecule." [Blum 1990]. When dopamine is released into the synapse, it stimulates a number of receptors (D1-D5), which results in increased feelings of well-being and stress reduction [Picetti 2013]. The mesocorticolimbic dopaminergic pathway plays an especially important role in mediating the reinforcement of natural rewards like food and sex, as well as unnatural rewards like drugs of abuse [Melis 2005]. Natural rewards include satisfaction of physiological drives (e.g., hunger and reproduction) and unnatural rewards are learned and involve satisfaction of acquired pleasures such as hedonic sensations derived from alcohol and other drugs, as well as from gambling and other risk-taking behaviors. [Blum 1996; Blum 2013; Blum 2014].

In discussing RDS, insensitivity and inefficiency in the reward system is specifically referred to. There may be a common neurocircuitry, neuroanatomy and neurobiology for multiple addictions and for a number of psychiatric disorders. [Bowirrat 2005]. Due to specific genetic antecedents and environmental influences (epigenetic) a deficiency of the D2 receptors may predispose individuals to a high risk for multiple addictive, impulsive, and compulsive behaviors. It is well known that alcohol and other drugs of abuse, as well as most positive reinforces (i.e., sex, food, gambling, aggressive thrills) cause activation and neuronal release of brain dopamine and involvement of the $Na^+/K^+$-ATPase. Dopamine release can decrease negative feelings and satisfy abnormal cravings for alcohol, cocaine, heroin and nicotine which among others are linked to low dopamine function. [Rothman 2007].

In doing association studies for which an investigator requires a representative control sample for a single RDS psychiatric diagnosis or for potential subsets of RDS, there are limitations that relate to controls poorly screened for multiple RDS behaviors and other related psychiatric disorders. Missing behaviors that are part of the RDS subset may be the reason for spurious results when genotyping for single subsets of RDS behaviors.

For example, an individual may not drink or use drugs but may have other RDS behaviors like overeating or intensive video gaming. In support of this notion, Blum et al. [Blum 2011] found a very strong association of the dopamine D2 receptor A1 allele (100%) in one Family (A). In addition, every individual in Family B also has at least one dopaminergic high risk allele (100%) (48% carried the DRD2 A1 allele]). Moreover, in family B only three adult individuals had no addictive behaviors. When this was compared with results in which 55 RDS subjects carried the DRD2 A1 allele at 78.2% with the results of Noble 2003 in which 597 severe alcoholics at (49.3%) carried the A1 allele, there was a significant difference between these two groups ($\chi^2$=16.9, p<0.001). This demonstrated that the A1 allele prevalence increases with multiple RDS behaviors.

SUMMARY OF THE INVENTION

The present invention satisfies the need to classify patients at genetic risk for drug/alcohol seeking behavior prior to or upon entry to residential and or non-residential chemical dependency and pain programs. This invention incorporates the utilization of an "allelic analysis," which is an analysis used to determine the presence of particular alleles in the tested subject. In an embodiment of the present invention, it has been discovered that there are at least eleven risk alleles associated with ten candidate genes. To determine risk severity, the percentage of prevalence of the risk alleles was determined using allelic analysis and a severity score based on percentage of these alleles was determined.

The genetic polymorphisms [DRD1=G; DRD2=A1; DRD3=C; DRD4=C; DAT1=9R; DRD4=7-11R; HTTLPR=S or L; MAOA=3.5-5R; COMT=G; OPRM1=G; and GABRB3=181] most associated with RDS risk were tested in 273 subjects. The percentage-prevalence of risk alleles were calculated and severity ranked in 273 subjects as: All subjects tested positive for risk severity, 40.4% (having 9 or more RDS risk alleles), 30.9% (7 or 8 RDS risk alleles), and 28.7% (6 or less RDS risk alleles). Without controlling for age or gender utilizing $\chi^2$ analysis, it was found that a significant predictive association between individuals with 7 or higher risk alleles and alcohol severity risk ($\chi^2$=8.38, df=1, p<0.004). Logistic regression results showed age (b=0.45, S.E.=0.11, Wald $\chi^2$=15.29, df=1, p<0.001) and having a greater number of RDS risk alleles (b=0.741, S.E.=0.29, Wald $\chi^2$=6.39, df=1, p=0.012) significantly predicted alcohol severity scores collected using the Addiction Severity Index Media Version (ASI-MV).

In general, in one aspect, the invention features a method of obtaining a risk score for evaluating stratification of a plurality of ranges for a genetic addiction risk. The method includes the step of obtaining a biological sample from a subject. The method further includes the step of performing an allelic analysis on the biological sample to determine the presence of a plurality of pre-determined alleles. Each of the alleles in the plurality of pre-determined alleles is associated with a gene in a plurality of pre-determined genes. There are at least ten genes in the plurality of pre-determined genes. There is at least one allele for each of the genes in the plurality of pre-determined genes. The method further includes the step of assigning a count for each of the alleles in the plurality of pre-determined alleles that was present in the biological sample. The method further includes the step of determining a risk score based upon the count, wherein the stratification of the plurality of ranges identifies a severity of the genetic addition risk.

Implementations of the inventions can include one or more of the following features:

The plurality of pre-determined alleles may include: (a) allele G of gene DRD1; (b) allele A1 of gene DRD2; (c) allele C of gene DRD3; (d) allele C of gene DRD4; (e) allele 9R of gene DAT1; (f) allele 7-11R of gene DRD4; (g) allele S or L of gene HTTLPR; (h) allele 4R of gene MAOA; (i) allele G of gene COMT; (j) allele G of gene OPRM1; and (k) allele 181 of gene GABRB3. These pre-determined alleles are the alleles of SEQ ID NOS 1-8, DAT1 3' 40 bp repeat, DRD4 48 bp repeat in intron 3, and GABARB3 (CA-dinucleotide repeat). In some instances, the DAT1 3' 40 bp repeat, DRD4 48 bp repeat in intron 3, and GABARB3 (CA-dinucleotide repeat) are as disclosed in Kirchheiner 2007, Johnson 2008, and Feusner 2001, respectively.

The risk score in a first range can be indicative of a low genetic addictive risk. The risk score in a second range can be indicative of a moderate genetic addictive risk. The risk score in the third range can be indicative of a high genetic addictive risk.

For the genetic addictive risk for drugs, the high range can be 4 and above.

For the genetic addictive risk for drugs, the low range can be from 0 to 1.

For the genetic addictive risk alcohol, the high range can be 8 and above.

For the genetic addictive risk for alcohol, the low range can be from 0 to 3.

The risk score can be the sum of the alleles in the plurality of pre-determined alleles found to be present in the biological sample.

The step of determining the risk score does not include weighting results of the allelic analysis of the biological sample.

The risk score can identify the stratification of a reward deficiency syndrome selected from the group consisting of alcohol, psycho-stimulants, marijuana, nicotine, opiates, epigenetic induced altered opiate receptor function, carbohydrates, obesity, gambling, sex addiction, aggression, stress, personality disorders, and novelty seeking, ADHD, Tourette's syndrome, Autism, and combinations thereof.

In general, in another aspect, the invention features a method that includes a genotypic analysis of a panel of genes to identify a plurality of alleles. The plurality of alleles includes: (a) allele G of gene DRD1; (b) allele A1 of gene DRD2; (c) allele C of gene DRD3; (d) allele C of gene DRD4; (e) allele 9R of gene DAT1; (f) allele 7-11R of gene DRD4; (g) allele S or L of gene HTTLPR; (h) allele 4R of gene MAOA; (i) allele G of gene COMT; (j) allele G of gene OPRM1; and (k) allele 181 of gene GABRB3.

In general, in another aspect, the invention features a kit for analyzing a panel of genes that includes primers for sequencing (5' to 3') consisting of (a) allele G of gene DRD1; (b) allele A1 of gene DRD2; (c) allele C of gene DRD3; (d) allele C of gene DRD4; (e) allele 9R of gene DAT1; (f) allele 7-11R of gene DRD4; (g) allele S or L of gene HTTLPR; (h) allele 4R of gene MAOA; (i) allele G of gene COMT; (j) allele G of gene OPRM1; and (k) allele 181 of gene GABRB3.

In general, in another aspect, the invention features a method of establishing a genetic risk stratification of a plurality of ranges for genetic addictive risk analysis. The method includes the step of selecting a plurality of alleles. Each of the alleles in the plurality of alleles is associated with a gene in a plurality of genes. There are at least ten genes in the plurality of genes. There is at least one allele for each of the genes in the plurality of genes. The method further includes the step of performing an allelic analysis using the plurality of alleles on a plurality of subjects. The plurality of subjects includes a statistically informative sample of subjects. Each of the subjects in the plurality of subjects have a non-allelic risk score. The non-allelic risk score having been determined independent of the allelic analysis. The method further includes the step of assigning a count for each of the alleles in the plurality of pre-determined alleles that was present in the biological sample. The method further includes the step of determining an allelic risk score for each subject in the plurality of subjects based upon the count. The method further includes the step of comparatively analyzing the non-allelic risk scores and the allelic risk scores. The comparative analysis results in establishing that the allelic risk score significantly predicts the non-allelic score of the plurality of subjects. The significant prediction is at a p-value of at most 0.05.

Implementations of the inventions can include one or more of the following features:

The p-value can be at most 0.01.

At least five of the alleles in the plurality of alleles can be selected from the group consisting of (a) allele G of gene DRD1; (b) allele A1 of gene DRD2; (c) allele C of gene DRD3; (d) allele C of gene DRD4; (e) allele 9R of gene DAT1; (f) allele 7-11R of gene DRD4; (g) allele S or L of gene HTTLPR; (h) allele 4R of gene MAOA; (i) allele G of gene COMT; (j) allele G of gene OPRM1; and (k) allele 181 of gene GABRB3.

At least eight of the alleles in the plurality of alleles can be selected from the group consisting of (a) allele G of gene DRD1; (b) allele A1 of gene DRD2; (c) allele C of gene DRD3; (d) allele C of gene DRD4; (e) allele 9R of gene DAT1; (f) allele 7-11R of gene DRD4; (g) allele S or L of gene HTTLPR; (h) allele 4R of gene MAOA; (i) allele G of gene COMT; (j) allele G of gene OPRM1; and (k) allele 181 of gene GABRB3.

The step of comparatively analyzing can include utilizing logistic regression modeling.

The non-allelic risk score can be based upon stratification of a reward deficiency syndrome selected from the group consisting of alcohol, psycho-stimulants, marijuana, nicotine, opiates, epigenetic induced altered opiate receptor function, carbohydrates, obesity, gambling, sex addiction, aggression, stress, personality disorders, and novelty seeking, ADHD, Tourette's syndrome, Autism, and combinations thereof.

DETAILED DESCRIPTION

The present invention relates to methods and kits for assessing severity index for alcohol abuse, drug abuse, and other reward deficiency syndromes. In terms of a single subtype of RDS (such as alcoholism or even psychostimulant abuse), there are problems in using a single diagnosis. Instead, a new strategy for population-based studies has been discovered in which the investigator requires a representative control sample, removing confounding cases from the control group that may improve chances of finding significant differences between experimental and control groups. This approach however may risk a "lack of representation' in the control group." Even the use of stratified samples (weighting samples) may not be good enough. Super controls has been criticized by some on the grounds that their relatives will have rates of co-morbid disorders lower than that in the general population and may produce spurious co-aggregation of disorders within families. This argument is valid only if the same psychopathology that is removed from the control group is not excluded from among the probands and their relatives. This provides the rationale to encourage others to begin to carefully select true controls especially when dealing with complex traits such as RDS.

In the case of finding a "pure" phenotype, especially in the psychiatric arena, it is unknown whether nature truly carved out the psychiatric disorders in the same fashion as is seen in the DSM-V. This is true because behaviors are very complex, whereby specific genes for behavioral tendencies (anxiety, impulsivity, compulsivity, harm avoidance, aggressiveness, addiction, etc.) only accounts for a small risk contribution to the overall phenotype. Therefore, there must be a shift in the emphasis to the "systems biological" approach, which takes into account the inter relationship of dysfunctional behaviors, the polygenic nature of psychiatric disorders, and the environment (epigenetic).

The established concept of RDS must be considered to help define this complex array of behaviors, and associated molecular dysfunctions. Victims of RDS carry polymorphic genes in dopaminergic pathways that results in hypo-dopaminergic function caused by a reduced number of dopamine D2 receptors, reduced synthesis of dopamine (dopamine beta-hydroxylase), reduced net release of presynaptic dopamine, increased synaptic clearance due to a high number of dopamine transporter sites and low D2 receptor densities making them more vulnerable to addictive activities.

The need for a unified set of related symptoms in the affected phenotype is important not only for population-based association studies, but also for linkage analysis. The RDS concept involves, shared genes and behavioral tendencies including dependence on alcohol, psycho-stimulants, marijuana, nicotine (smoking), opiates, epigenetic induced altered opiate receptor function, carbohydrates (sugar-binging), obesity, pathological gambling, sex addiction, aggression, stress, certain personality disorders, and including novelty seeking. While there are poly-genes involved the common theme in all of these substances and behaviors is that they induce pre-synaptic dopamine release at the NAc. Spectrum disorders such as ADHD, Tourette's syndrome and Autism are included due to dopamine dysregulation.

A screened control group is essential for uncovering population-based associations where the disease in question may be very common. It is known that approximately one-third of the population meet lifetime criteria for common psychiatric disorders according to the results of the Epidemiological Catchment Area (ECA) survey. Since RDS is a "polygenic disorder" involving multiple genes and many polymorphisms and requires a threshold number of polygenes, unaffected individuals in the population also carry some of these genes. The dopamine D2 receptor gene (A1 allele) is present in about one-third of unscreened Americans (29.4% in 3329 subjects studied up until 2003). [Blum 2000].

Genetic Addiction Risk Assessment

Applicant has discovered that a multifaceted non-specific RDS behaviors should be considered as the true "reward" phenotype (endophenotype) instead of a single subset RDS behavior such as alcoholism. This may be a paradigm shift in future association and linkage studies.

Very few behaviors depend upon a single gene. Complexes of genes (polygenic) drive most of the populations' heredity-based behaviors, suggesting that genetic panels or algorithms organized into genetic indexes, such as Genetic Addiction Risk Assessment, can be valuable clinically to determine risk. Certainly abnormal functions of these brain systems can be due to specific genetic factors interacting with environmental factors and understanding the interactions of these components is likely to lead to better treatment.

While there have been other reports that help establish the RDS concept, there are many genes and SNPs involved in developing a true Genetic Addiction Risk Assessment.

The results of this may have direct implications for both the diagnosis and targeted treatment of RDS behaviors by analyzing the association of these reward genes and RDS behaviors. This underscores the potential involvement of at least D2 receptor dysfunction as an important genetic antecedent to addiction as a disease but not as the only risk gene. In keeping with the theory of common neurogenetic mechanisms, it is now believed by Applicant that RDS is a basic phenotype covering many reward behaviors and pertinent psychiatric disorders including spectrum disorders that should be included in the future in DSM as a genetic umbrella for many psychiatric diagnoses. In fact most recently RDS has been accepted as an important psychiatric disorder by SAGE publication and will appear in the Encyclopedia of Abnormal Psychology (2015). The reward genes have been extensively studied and include, but are not limited to D1-D5 receptors; Dopamine Transporter (DAT1); Serotonin 2a/c receptors; Serotonin transporter (5-HTTLPR); Mu opiate receptor (OPRM1); GABA receptor (GABRB3); catechol-o-methyltransferase (COMT) val158met; and MAO-A gene promoter VNTR among others. See TABLE 2.

TABLE 2

Advanced Genetic Addiction Risk Analysis Panel of Reward Genes

| | |
|---|---|
| Dopamine D1 Receptor Gene | Mu-opiate Receptor Gene |
| Dopamine D2 Receptor Gene | GABA -B3 Receptor Gene |
| Dopamine D3 Receptor Gene | PENK Gene |
| Dopamine D4 Receptor Gene | Monoamine Oxidase A Gene |
| | Catechol-O-Methyltransferase Gene |
| Serotonin 2a Receptor | Cytochrome P450 Gene Network |
| Gene Serotonin Transporter Gene | NMDA receptor Gene |

Applicant has discovered that evaluating using a polygenic test to determine stratified genetic risk of addictive patients entering treatment facilities suggest a paradigm shift in providing important information about an individual's predisposition to RDS based on a number of risk alleles. Validation of these results provides an impetus for appropriate and careful selection of a complete Gene Map for all addictive behaviors.

While there has been a plethora of research on many reward gene polymorphisms and RDS risk including drugs and alcohol, there has not been a quantitative analysis revealing a method by which counting risk alleles result in a significant predictor of addiction severity. In fact, there has been a continual controversy concerning what if any candidate genes will actually predict severity. In earlier patents (such as U.S. Pat. No. 6,955,873, issued to Blum and other patent application suggested from 32 to hundreds of genes.

A panel of genes and associated alleles have been discovered. This panel has shown to significantly predict clinical outcomes as determined by the self-reported ASI-Media version instrument. A pencil and paper test mandated in thirteen states across the United States and in many countries worldwide. As compared to TABLE 2 above (which that refers to a generalized list of reward genes), the panel includes the analysis of the genes and corresponding alleles set forth in TABLE 3.

TABLE 3

Genetic Addiction Risk Assessment Panel

| Sequence ID No | Gene/Genotype | Location/Genotype | Risk Allele |
|---|---|---|---|
| SEQ ID NO 1 | MAOA-uVNTR (3' 30 bp repeat) | +nnnnn 3' 30 base-pair Repeat (R) on X chromosome only | 3.5-5R |
| | DAT1 (3' 40 bp repeat) | +nnnnn 3' 40 Base-Pair Repeat (R) ≤9R is short, >9R is long | 9R |
| | DRD4 (Intron 3 48 bp repeat) | +nnnn Intron 3, 48 base-pair Repeat (R) <7R is short, >7R is long | 7R+ |
| SEQ ID NO 2 | 5HTTLPR (43 bp 5' ins/del) + rs25531 | +nnnnn 43 base-pair 5' insertion/deletion | S or L |
| SEQ ID NO 3 | rs4532, DRD1 | +48 A > G | G |
| SEQ ID NO 4 | rs1800497, DRD2 TaqI A1 | +nnnnn A > G | A1 |
| SEQ ID NO 5 | rs6280, DRD3 (Gly-Ser) | +nnnnn C > T | C |
| SEQ ID NO 6 | rs1800955, DRD4 -521 C/T | -521 C > T | C |
| SEQ ID NO 7 | rs4680, COMT (Val-Met) | +nnnnn A > G | G |
| SEQ ID NO 8 | rs1799971, OPRM1 (Asn-Asg) | +nnnnn A > G | G |
| | GABRB3 (CA-dinucleotide repeat) | +nnnn CA-Repeat (171-201) | 181 |

No one has ever previously reported an analysis focusing upon this combination of genes and respective alleles. In fact, any change in this list has shown to render this analysis into a non-significant predictor.

In one embodiment, the DAT1 genotype is the DAT1 3' 40 bp repeat disclosed in Kirchheiner 2007.

In one embodiment, the DRD4 genotype is the DRD4 48 bp repeat in intron 3 disclosed in Johnson 2008.

In one embodiment, the GABARB3 CA-dinucleotide repeat is disclosed in Feusner 2001.

Sampling

Participants were identified and enrolled in partnership with Inflexxion and eight geographically dispersed treatment centers located in the United States. The eight treatment centers included: Addiction Recovery Resource, Catholic Charities of Maine, Center for Psychiatric Medicine, G & G Holistic Addiction Treatment Center, Integrative Life Center, Malibu Beach Recovery Center, and Meadows Edge Recovery Center and Tennessee treatment center. In agreement with INGENE, LLC (Austin, Tex.) and Dominion Diagnostics (North Kingstown, R.I.), each treatment center agreed to identify, consent, and enroll 40 subjects. Study protocols were reviewed and approved by the University of Vermont, School of Medicine (Burlington, Vt.), and PATH Foundation (NY) Institutional Review Boards (IRB). For the patient protection the genotyping data by the Institute for Behavioral Genetics (IBG), University of Colorado Boulder, Boulder, Colo. Specimen tubes were labeled with a pre-defined ID and bar coded by Dominion Diagnostics in order to limit sampling errors. Subjects supplied 2 ml of saliva that was stabilized using a buffer consisting of sodium dodecyl sulfate, TRIS-EDTA buffer, pH 8.0 and proteinase K. Tubes were stored at room temperature at each treatment center and shipped to Dominion Diagnostics after they had enrolled 40 subjects. Patent saliva samples were then sent to AS at IBG for DNA extraction and isolation using protocols detailed elsewhere (74-Haberstick et al, 2014).

Genotyping

An index of the genes included in the genetic addiction risk score panel and the specific risk polymorphisms are provided in TABLE 4. Each genetic variant or polymorphism was selected on the basis of RDS and known contribution to a state of low dopaminergic or hypodopaminergic functioning in the brain reward circuitry.

TABLE 4

Genetic Addiction Risk Scale Genotype Panel

| Polymorphism | Gene | Variants | Risk Allele |
|---|---|---|---|
| Single Nucleotide Polymorphisms (SNPs) | | | |
| rs4532 | Dopamine D1 Receptor (DRD1) | A/G | G |
| rs1800497 | Dopamine D2 Receptor (DRD2) | A1 (A)/A2 (G) | A1 |
| rs6280 | Dopamine D3 Receptor (DRD3) | C/T | C |
| rs1800955 | Dopamine D4 Receptor (DRD4) | C/T | C |
| rs4680 | Catechol-O-Methyltransferase (COMT) | A (Met)/G (Val) | G |
| rs1799971 | Mu-Opoid Receptor (OPRM1) | A (Asn40)/G (Asp40) | G |
| Simple Sequence Repeats (Variable Number Tandem Repeats & Insertion/Deletions) | | | |
| 3' 40 base-pair Repeat | Dopamine Transporter Receptor (DAT1) | 9 Repeat (R) | 9R | was conformed to standard HIPPA and Genetic Information Non-Discrimination Act (GINA) practices mandated by law. The participants provided written informed consent.

Questionnaire and Biological Assessments

The subjects were interviewed and evaluated by a trained clinician for any substance dependency using a standard battery of diagnostic questionnaires and biological tests. Paper-and-pencil tests included the *Drug History Questionnaire and Symptom Severity Questionnaires* (73-Stranz & Welsh, 1995), and the *Addiction Severity Index*. Biological tests included: urine drug tests, breathalyzer test, and a blood based CBC test. Alcohol and drug use data was collected using the Addiction Survey Index-Multi-Media (ASI-MV).

Severity scores were determined using a proprietary algorithm developed by Inflexxion. Scores on the severity ratings could range between 'no real problem' (0) to 'extreme problem' (9) and included questions about lifetime drug use. Clinically, scores on the severity ratings scales were utilized for identifying drug use problems and treatment planning. In these data, ASI alcohol and drug severity scores were slightly skewed to the left (Alcohol: skewness=−0.211, kurtosis=−1.473; Drugs: skewness=−0.922, kurtosis=−0.483), and suggested that this sample of patients had a greater number of subjects with lower rather than higher alcohol scores.

Sample Collection & Chain of Custody

Saliva was collected using a minimally invasive process that requires a subject to spit into a collection tubes supplied The assays for Amelogenin, MAOA-uVNTR, DRD4, DAT1 and 5HTTLPR [were done in a single multiplex PCR reaction consisting of two µl of DNA (20 ng or less), 1.8 mM $MgCl_2$, 180 µM each deoxynucleotide (dNTP, NEB), with 7'-deaza-2'-deoxyGTP (deaza-GTP, Roche Applied Science, Indianapolis, Ind.) substituted for one-half of the dGTP, 10% DMSO, forward (fluorescently labeled) and reverse primers (sequences and concentrations in TABLE 5, one unit of AmpliTaq Gold® polymerase (Life Technologies Grand Island, N.Y.) and 1× PCR buffer II in a total volume of 20 µl. The assay for the dinucleotide repeat in GABRB3 was analyzed separate in a PCR reaction consisting of two µl of DNA (20 ng or less), 2.5 mM $MgCl_2$, 200 µM each deoxynucleotide (dNTP, NEB), forward (fluorescently labeled) and reverse primers, one unit of AmpliTaq Gold® polymerase and 1×PCR buffer II in a total volume of 20 µl. Amplifications were performed using a modified touchdown PCR method. [Anchordoquy 2003; Don 1992] A 95° C. incubation for 10 min was followed by two cycles of 95° C. for 30 s, 65° C. for 30 s, and 72° C. for 60 s. The annealing temperature was decreased every two cycles from 65° C. to 57° C. in 2° C. increments (10 cycles total), followed by 30 cycles of 95° C. for 30 s, 55° C. for 30 s, and 72° C. for 60 s, a final 30-min incubation at 72° C. and a hold at 4° C. Each 96 well plate included non-template and DNA standards of known genotype.

TABLE 5

Marker, Primer, and Resulting Size Ranges of polymorphisms characterized

| Gene | Sequence (5' → 3') | Conc. (nM) | Size Range (bp) |
|---|---|---|---|
| Amelogenin-F | NED-CCC TGG GCT CTG TAA AGA ATA GTG | 300 | 103, 109 |
| Amelogenin-R | ATC AGA GCT TAA ACT GGG AAG CTG | 300 | (X, Y) |
| MAO-uVNTR-F | 6FAM-ACA GCC TGA CCG TGG AGA AG | 200 | 291-381 |
| MAO-uVNTR-R | GAA CGG ACG CTC CAT TCG GA | 200 | (2R-5R) |
| DAT1-F | 6FAM-TGT GGT GTA GGG AAC GGC CTG AG | 300 | 200-600 |
| DAT1-R | CTT CCT GGA GGT CAC GGC TCA AGG | 300 | (3R-13R) |
| DRD4-F | VIC-GCT CAT GCT GCT GCT CTA CTG GGC | 600 | 279-711 |
| DRD4-R | CTG CGG GTC TGC GGT GGA GTC TGG | 600 | (2R-11R) |
| 5HTTLPR-F | NED-ATG CCA GCA CCT AAC CCC TAA TGT | 600 | 376, 419-549 |
| 5HTTLPR-R | GGA CCG CAA GGT GGG CGG GA | 600 | (S, L-XL) |
| 5HTTLPR-Hu-F | 6FAM-GCA ACC TCC CAG CAA CTC CCT GT | 500 | 138, 181 |
| 5HTTLPR-Hu-R | GAG GTG CAG GGG GAT GCT GGA A | 500 | (S, L) |
| GABRB3-F | 6FAM-CTC TTG TTC CTG TTG CTT TCA ATA CAC | 500 | 171 - 201 |
| GABRB3-R | CAC TGT GCT AGT AGA TTC AGC TC | 500 | |

TABLE 6

Sequences of certain polymorphisms used in to the methods of the present invention

| Polymorphism | Sequence |
|---|---|
| MAOA-uVNTR | ACCGGCACCGGCACCAGTACCCGCACCAGT |
| rs25531 | CTCGCGGCATCCCCCCTGCACCCCC[A/G]GCATCCCCCCTGCAGCCCCCCAGC |
| rs4532 | GGGGCTCTGACACCCCTCAAGTTCC[C/T]AAGCAGGGAATAGGGGTCAGTCAGA |
| rs1800497 | TGGACGTCCAGCTGGGCGCCTGCCT[C/T]GACCAGCACTTTGAGGATGGCTGTG |
| rs6280 | GCCCCACAGGTGTAGTTCAGGTGGC[C/T]ACTCAGCTGGCTCAGAGATGCCATA |
| rs1800955 | GGGCAGGGGGAGCGGGCGTGGAGGG[C/T]GCGCACGAGGTCGAGGCGAGTCCGC |
| rs4680 | CCAGCGGATGGTGGATTTCGCTGGC[A/G]TGAAGGACAAGGTGTGCATGCCTGA |
| rs1799971 | GGTCAACTTGTCCCACTTAGATGGC[A/G]ACCTGTCCGACCCATGCGGTCCGAA |

A description of the assay for rs25531 (A/G) is detailed elsewhere [Haberstick 2014]. This SNP is located in the Long-form of the 5HTTLPR and allows determination of the $L_A$ and $L_G$ alleles. The 5HTTLPR site containing the SNP was amplified in a single PCR reaction composed as described above with the primers described in Hu 2005. The cycling conditions were a 95° C. incubation for 10 min followed by two cycles of 95° C. for 30 s, 65° C. for 30 s, and 72° C. for 60 s, two cycles of 95° C. for 30 s, 63° C. for 30 s, and 72° C. for 60 s, 30 cycles of 95° C. for 30 s, 61° C. for 30 s, and 72° C. for 60 s, a final 30-min incubation at 72° C. and a hold at 4° C. Following PCR amplification the PCR products were incubated [Wendland 2006] with five units of MspI (NEB, Ipswitch, Mass.) for 90 min at 37° C. A 97 bp restriction digest fragment is indicative of the $L_G$ allele. For the genetic addiction risk score coding, two combined alleles were reported: the S' which consists of S, and $L_G$ alleles and L' which consists of $L_A$ and extra-long alleles. Note that the S' and L' refer to composed activity bins and that these are not individual alleles per se. Each 96 well plate included non-template and DNA standards of known genotype.

After amplification, PCR products and MspI digests were filter purified using Zymo Research (Irvine, Calif.) ZR-96 DNA Sequencing Clean-up Kits following manufacturer's directions. An aliquot of PCR products was combined with loading buffer containing size standard (Rox1000, Gel Company, San Francisco, Calif.) and analyzed with an ABI PRISM® 3130xl Genetic Analyzer (Life Technologies) using protocols supplied by the company. Data were analyzed with Genemapper software and the resulting allele sizes independently reviewed by two investigators.

The SNP assays for TaqIA (rs1800497), COMT val158met (rs4680), DRD1 (rs4532), DRD3 (rs6280), DRD4-521C/T (rs1800955) and OPRM1 (rs1799971) were done using a fluorogenic 5' nuclease (Taqman®, ABI, Foster City, Calif.) method [Haberstick 2004] on an ABI Prism® 7000 Sequence Detection System via the allelic discrimination mode. [Livak 1999].

Reactions containing 20 ng of DNA were performed in 15 µl reactions with TaqMan® Universal PCR Master Mix using the standard cycling conditions. Primer and probe concentrations were 900 µM and 200 µM, respectively. Sequences of the TaqIA and COMT primers and probes are probes are provided in TABLE 7. All remaining assays were ordered directly from Life Technologies. Each 96 well plate included non-template and DNA standards of known genotype.

TABLE 7

Probe and Primer Sequences for COMT val158met and DRD2 Taq1A Polymorphisms

| Gene | Probe/Primer | Sequence (5'→3') |
|---|---|---|
| COMT | T (met) probe | VIC-ACCTTGTCCTTCATGCCAGCGAAAT-NFGMGB |
|  | C (val) probe | FAM-CCTTGTCCTTCACGCCAGCGA-NFQMGB |
|  | Forward Primer | TCGAGATCAACCCCGACTGT |
|  | Reverse Primer | AACGGGTCAGGCATGCA |
| DRD2 | T (A1) probe | VIC-CCTGCCTTGACCAGC-NFQMGB |
|  | C (A2) probe | FAM-CTGCCTCGACCAGC-NFQMGB |
|  | Forward Primer | GTGCAGCTCACTCCATCCT |
|  | Reverse Primer | GCAACACAGCCATCCTCAAAG |

Statistical Analysis

Mean, standard deviations, chi-square and regression tests were performed using SPSS (Version 21.0). Fischer Exact Tests were used to test whether there were significant differences between the dichotomized alcohol and drug severity risk scores. For alcohol, scores at or below the mean of 4.65 were considered 'low' (0) while scores above the mean were considered 'high' (1). For drug severity scores, scores at or below 4 were considered 'low' (0) while scores above were considered 'high' (1). Regression analyses were used to examine the association between the genetic risk score and severity risk score measures, adjusting for sex (female=0, male=1) and age (continuous). Though, scores on both the alcohol and drug severity risk scales were slightly skewed towards lower values, the impact of square-root and log-transformations on the distribution of scores was examined. Along a priori lines, risk alleles were assigned a score of 1. An individual's genetic risk score was the sum of all risk alleles for that individual.

The percentage-prevalence of risk alleles was calculated and severity ranked in 273 subjects as: All subjects texted positive for risk severity, 40.4% (having 9 or more RDS risk alleles), 30.9% (7 or 8 RDS risk alleles), and 28.7% (6 or less RDS risk alleles).

Hardy Weinberg equilibrium (HWE) was confirmed for each gene using $\chi^2$ tests.

Example No. 1

In an embodiment of the present invention, an analysis was performed for genetic risk stratification for Reward Deficiency Syndrome (RDS). The genetic polymorphisms [DRD1=G; DRD2=A1; DRD3=C; DRD4=C; DAT1=9R; DRD4=7-11R; HTTLPR=S or L; MAOA=3.5-5R; COMT=G; OPRM1=G; and GABRB3=181] were tested in 393 participants (or subjects) of which 273 of these subjects completed the questionnaire and biological assessments.

Without controlling for age or gender utilizing $\chi^2$ analysis, a significant predictive association was found between individuals with 7 or higher risk alleles and alcohol severity risk ($\chi^2=8.38$, df=1, p<0.004). Logistic regression results showed age (b=0.45, S.E.=0.11, Wald $\chi^2=15.29$, df=1, p<0.001) and having a greater number of RDS risk alleles (b=0.741, S.E.=0.29, Wald $\chi^2=6.39$, df=1, p=0.012) significantly predicted alcohol severity scores collected using the Addiction Severity Index Media Version (ASI-MV). Similar experiments were achieved for the ASI-Drug (opioids and psychostimulants) severity risk score as well.

A low p-value (less than 0.05) is highly significant. The above results were particularly robust, as the p-values observed were around 0.01 and better. This is indicative that a relationship exists between the risk assessment generated from the cluster being tested and the risk severity of the group being investigated.

Comparative Examples (Changing of Alleles)

The alleles of this tested panel (or cluster) was further evaluated by change a specific risk allele in the cluster as set forth in Example No. 1. The resultant data revealed a non-significant association with the ASI-Media version for alcohol severity.

It was found that when the risk allele for the MAOA=3R was evaluated instead of the 4R (and keeping the other alleles of the cluster the same as in the example set forth above), no significant association was obtained (p=0.819).

A similar finding was obtained for the COMT risk allele changing from the Val/met to the met/met (again keeping the other alleles of the cluster the same as in the example set forth above) whereby no significance was obtained in terms of association with alcohol severity predicted by the ASI-Media version (p=0.634).

It was also found that significance was lost when the risk allele of the DAT1 was switched from the 9R to the 10R (p=0.728) (again keeping the other alleles of the cluster the same as in the example set forth above).

It is also important that the analysis was predictive of alcohol severity when the subject carried 8 or more risk alleles. Testing 7; 6; 5; 4; 3; 2 and 1 did not predict risk. Similar findings were obtained for drug severity prediction except cut off was 4 and above as a predictor.

Comparative Examples (Weighting)

In terms of weighting the genes and alleles, whereby the value of each risk allele may display a more powerful risk was also evaluated using the same dataset. Standard weighting involves utilizing super controls against the ASI-Alcohol severity index as well as drug severity index. In this method the resultant odds ratios (OR) issue used to determine the appropriate algorithm for weighting each representative gene allele.

Since no super controls were used (no RDS behaviors in pro and in family), a number of genes that appeared to be more important to others in terms of for example relapse and drug reinstatement were evaluated.

For example, the DRD2 A1 allele has been found to be significantly involved in relapse, mortality, and hospitalization. Previous studies involving association to addictive behaviors had identified a significance with only A1. Accordingly, the score value for a positive indication of the DRD2 A1 allele was given a value of 2 (instead of a score of 1 as previously scored in Example No. 1 for all positive indications of an allele). When this one weighing was done (and all other alleles remained weighted with a score of 1 for a positive indication), the results was less significant than in the Example, having a p-value equal to 0.059 (p=0.059). P-values were determined as set forth in $X^2$ analysis.

Repeating this weighting for only the COMT gene/allele resulted in a similar finding (p=0.600). Further, repeating this weighting for only the DAT1 gene also showed that the results were less significant (p=0.154).

These comparative analysis data show that weighting of the allele analysis results (i.e., relative to one allele to the others) is not as significant as the combination of testing that is occurring within the cluster of genes/alleles. It is believed that an analysis with super controls may provide weighting of one or more of the genes/alleles; however, such weighting is not required. This further indicates the counting technique of risk alleles without the need for super controls.

Score Assessment

By this, it has now been a quantitation has been discovered that actually shows a predictive value when considering clinical outcome. It is one thing to evaluate for example drug and alcohol risk using case controls compared to single outcomes in terms of genetic polymorphisms but without actual prediction of clinical risk as determined by the ASI as one example, a list of genes and alleles is simply a guessing game.

thy that such ranges are not the same as those set forth above for the gene additive risks for drugs and alcohol. Rather, these provide a metric as to the percent of these alleles that a subject has in the panel, which alleles have been found to correlate with gene additive risks. Such normalized results thus provide a metric of where on the spectrum a subject falls, with the higher percentage indicating that the subject has a higher risk probability.

TABLE 8 shows a genetic addition risk test results having a risk score and normalized risk score indicated.

TABLE 8

Genetic Addiction Risk Score Test Results

| | PHYSICIAN | SPECIMEN | | PATIENT |
|---|---|---|---|---|
| Name:<br>Address: | Dr. X | Specimen Type:<br>Date Collected:<br>Time Collected:<br>Date Received:<br>Date Reported: | Name:<br>Date of Birth:<br>Accession ID:<br>Lab ID:<br>Gender: | Patient Y |

| Gene | Location/Genotype | Risk Allele | Result | Risk Allele Count |
|---|---|---|---|---|
| Single Nucleotide Polymorphisms (SNPs) | | | | |
| COMT | +nnnnn A > G | G | G, G | 2 |
| DRD1 | +48 A > G | G | A, A | 0 |
| DRD2 | +nnnnn A > G | A | A, A | 2 |
| DRD3 | +nnnnn C > T | C | C, T | 1 |
| DRD4 | −521 C > T | C | C, T | 1 |
| OPRM1 | +nnnnn A > G | G | G, A | 1 |
| Variable Number Tandem Repeats & Insertion/Deletions | | | | |
| DAT1 | +nnnnn 3' 40 Base-Pair Repeat (R) ≤9R is short, >9R is long | 9R | S, L | 1 |
| DRD4 | +nnnn Intron 3, 48 base-pair Repeat (R) <7R is short, >7R is long | >7, 8, 9, 10 or 11 (R) | S, L | 1 |
| 5HTTPLPR | +nnnnn 43 base-pair 5' insertion/deletion | S or L | S', S' | 2 |
| MAOA | +nnnnn 3' 30 base-pair Repeat (R) on X chromosome only | 4R | 5R | 0 |
| Dinucleotide Repeats | | | | |
| GABRA3 | +nnnn CA-Repeat (171-201) | 181 | 181, 194 | 1 |
| | | Risk Allele Count | | 12 out of possible 22 |
| | | RISK SCORE<br>NORMALIZED RISK SCORE | | 12<br>0.55 |

Using the cluster set forth in TABLE 3, the tested subjects were classified in ranges of low, moderate, and high gene additive risks for drugs and alcohol. For instance, for this panel of alleles, a score in the ranges of 0 to 1, 2 to 3, and 4 and above, correspond to low, moderate, and high for gene additive risks for drugs. Further, for instance, for this panel of alleles, a score in the ranges of 0 to 3, 4 to 7, and 8 and above, correspond to low, moderate, and high for gene additive risks for alcohol.

It is further noted that the results of the allele analysis can be normalized, i.e., divide the score (or count) by the total possible score. This provides alternative ranges that can be classified as low, moderate, and high risk in view of the tested alleles. Such ranges would be, for example, 0 to 0.3, 0.31 to 0.59, and 0.6 to 1, and would be categorized as low, moderate, and high risk for the tested alleles. It is notewor- As seen in TABLE 8, the risk allele count is based upon the positive indication of the alleles in the panel tested. For instance, the allelic analysis for the sample showed that for allele G of gene COMT, the result was "G,G" which gives a count of 2. Further, the allelic analysis for the sample showed that for allele G of gene DRD1, the result was "A,A" which gives a count of 0. Also, for instance, the allelic analysis for the sample showed that for allele C of gene DRD3, the results was "C,T" which gives a count of 1. The risk counts obtained for each of the tested alleles were then added up to yield the risk score, which, as shown in the sample of TABLE 8 was 12. As the maximum risk score was 22 (since 11 alleles were tested), the normalized score was 0.55 (which is also shown in TABLE 8).

Such risk score of 12 is indicative of a patient having a high genetic addition risk for alcohol (because the risk score is above 8) and a high genetic addiction risk for drugs (because the risk score is above 4). Such a normalized risk score of 0.55 (i.e., 55%) falls in the category of being a modest addiction risk on the normalized scale (which is a more conservative analysis). This reflects that there are multiple stratifications that can be utilized to determine genetic addictive risks.

The assessment of low, moderate, and high risk groups is quantified by the score received by using the panel of alleles. If a cut-off of counting eight alleles and above was used, a significant prediction using the ASI-alcohol severity index was not obtained. Moreover, this was true even if Applicant adhered to a strict allelic count based on the above presented risk alleles as seen in TABLE 3. However, when the cut-off point of seven risk alleles was utilized highly significant associations were observed.

The fact that there are many risk alleles for a number of reward genes (especially for opiates as just one example), it was only when a process was used to identify a proper combination of genes and alleles (having a low p-value) that the relationship between this cluster and the risk score was found. It is a significant discovery that not only must a proper group of genes to test be selected, the proper alleles out of hundreds of SNPS must also be utilized.

By this process of selecting genes and further selecting alleles to test to obtain a score that corresponds to observable low, moderate, and high risk ranges (with low p-value), Applicant has been able to create a useful test that can be readily and easily applied.

As representative of the difficulty in selecting the proper group of genes and alleles, the following is indicative of testing for opiates.

In terms of for example pain sensitivity certain candidate genes have been studied. Candidate genes such as those for catechol-O-methyltransferase, melanocortin-1 receptor, guanosine triphosphate cyclohydrolase and mu-opioid receptor have been intensively investigated, and associations were found with sensitivity to pain as well as with analgesic requirements in states of acute and chronic pain. In contrast, the impact of genetic variants of drug-metabolizing enzymes on the response to pharmacotherapy is generally well described. Polymorphisms of the cytochrome P450 enzymes influence the analgesic efficacy of codeine, tramadol, tricyclic antidepressants and nonsteroidal anti-inflammatory drugs. Together with further candidate genes, they are major targets of ongoing research in order to identify associations between an individual's genetic profile and drug response (pharmacogenetics). Moreover, sensitivity and tolerance to morphine were determined in 2 strains of mice, BALB/cBy and C57BL/6By, their reciprocal F1 hybrids and seven of their recombinant inbred strains. Sensitivity was established based on locomotor activity following the administration of saline, 10 or 20 mg/kg of morphine hydrochloride while tolerance was established according to the "hot plate" method following the single or repeated administration of saline, 5, 10, or 20 mg/kg of morphine hydrochloride. Results indicate that both sensitivity and tolerance to morphine are genotype-dependent and their inheritance is characterized by dominance or partial dominance.

The most common treatment for opioid dependence is substitution therapy with another opioid such as methadone. The methadone dosage is individualized but highly variable, and program retention rates are low due in part to non-optimal dosing resulting in withdrawal symptoms and further heroin craving and use. Methadone is a substrate for the P-glycoprotein transporter, encoded by the ABCB1 gene, which regulates central nervous system exposure. ABCB1 genetic variability influenced daily methadone dose requirements, such that subjects carrying 2 copies of the wild-type haplotype required higher doses compared with those with 1 copy and those with no copies (98.3+/−10.4, 58.6+/−20.9, and 55.4+/−26.1 mg/d, respectively; P=0.029). In addition, carriers of the AGCTT haplotype required significantly lower doses than non-carriers (38.0+/−16.8 and 61.3+/−24.6 mg/d, respectively; P=0.04). Although ABCB1 genetic variability is not related to the development of opioid dependence, identification of variant haplotypes may, after larger prospective studies have been performed, provide clinicians with a tool for methadone dosage individualization. Studies of polymorphisms in the mu opioid receptor gene, which encodes the receptor target of some endogenous opioids, heroin, morphine, and synthetic opioids, have contributed substantially to knowledge of genetic influences on opiate and cocaine addiction. Other genes of the endogenous opioid and monoaminergic systems, particularly genes encoding dopamine beta-hydroxylase, and the dopamine, serotonin, and norepinephrine transporters have also been implicated.

Moreover, genetically caused inactivity of cytochrome P450 (CYP) 2D6 renders codeine ineffective (lack of morphine formation), slightly decreases the efficacy of tramadol (lack of formation of the active O-desmethyl-tramadol) and slightly decreases the clearance of methadone. MDR1 mutations often demonstrate pharmacogenetic consequences, and since opioids are among the P-glycoprotein substrates, opioid pharmacology may be affected by MDR1 mutations. The single nucleotide polymorphism A118G of the mu opioid receptor gene has been associated with decreased potency of morphine and morphine-6-glucuronide, and with decreased analgesic effects and higher alfentanil dose demands in carriers of the mutated G118 allele. Genetic causes may also trigger or modify drug interactions, which in turn can alter the clinical response to opioid therapy.

For example, by inhibiting CYP2D6, paroxetine increases the steady-state plasma concentrations of (R)-methadone in extensive but not in poor metabolizers of debrisoquine/ sparteine. So far, the clinical consequences of the pharmacogenetics of opioids are limited to codeine, which should not be administered to poor metabolizers of debrisoquine/ sparteine. Genetically precipitated drug interactions might render a standard opioid dose toxic and should, therefore, be taken into consideration. Mutations affecting opioid receptors and pain perception/processing are of interest for the study of opioid actions, but with modern practice of on-demand administration of opioids their utility may be limited to explaining why some patients need higher opioid doses; however, the adverse effects profile may be modified by these mutations. Nonetheless, at a limited level, pharmacogenetics can be expected to facilitate individualized opioid therapy. It has been demonstrated that the muOR 304G variant significantly reduces intrathecal fentanyl ED(50) for labor analgesia, suggesting women with the G variant may be more responsive to opioids and require less analgesic drugs. These findings for intrathecal fentanyl pharmacogenetics may have implications for patients receiving opioids in other settings.

The following is a sampling of genes involved in the addictive process that can be informative relates to opiate addiction:

Mu opioid receptor, delta-opioid receptor; the metabotropic receptors mGluR6 and mGluR8, nuclear receptor NR4A2 and cryptochrome 1 (photolyase-like), DRD gene (D1-D5), Dat1, DBH, proenkephalin (PENK) and prodynorphin (PDYN), CAMKII; GnRH: CYP2D6; BDNF; NT-3 genes; GABA receptor subunit genes on 5q33; GABA(A) gamma2; OPRM1; G-protein alpha subunits; OPRK1; alpha2-adrenoceptor; TTC12; ANKK1; NCAM1; ZCRB1; CYP2B6; CYP2C19; CYP2C9; interleukin-2; RGS-R7; Gbeta5; MAO-A; 287 A/G polymorphism of catechol-O-methyltransferase; serotonin transporter; Ca2+/cAMP responsive element binding protein; CNR1; ABCB1, P-glycoprotein, UGT2B7, and CREB.

Such polymorphisms include a polymorphism in a gene encoding a Beta-adrenergic receptor; a polymorphism in a gene encoding an angiotensin converting enzyme (ACE); a polymorphism in a gene encoding an angiotensin 11 T1 receptor; a polymorphism in a gene encoding cholesteryl ester transfer protein; a polymorphism in a gene encoding a potassium channel; a polymorphism in a gene encoding a cytochrome P-450 enzyme, optionally CYP2D6; a polymorphism in a gene encoding a protein product of the HER2/neu oncogene; a polymorphism of the C825T gene; a polymorphism in the APOE gene locus); a polymorphism in the CT or TT allele of the dopamine D2 receptor gene; a SNP (polymorphism) designated AA, at nucleotide position-6 of the ANG gene; a polymorphism in a gene encoding Apo-A1; a polymorphism in a gene encoding Methylene Tetrahydrofolate Reductase (MTHFR), optionally a C677T polymorphism; a polymorphism in tumor necrosis factor (TNF) gene; a polymorphism in the carbohydrate responsive element-binding protein (ChREBP) gene; a polymorphism of the Leptin receptor gene; a polymorphism of the dopamine D2 receptors gene (DRD2); a polymorphism of any of the dopamine D1, D3, D4, and D5 genes; a dopamine D2 receptor polymorphism selected from the group consisting of Ser311 cys and Taq1A; a polymorphism in a c-fos gene; a polymorphism in the c-jun gene; a polymorphism in the c-myc, gene; a polymorphism in a gene encoding Sterol Regulatory Element Protein-1 (SREBP-Ic); a polymorphism in a gene encoding mitochondrial glycerol-3-phosphate acetyltransferase gene (MGPAT); a polymorphism in a gene encoding the peroxisome proliferator-activated receptor (PPAR-gamma-2) gene; the Pro12Ala polymorphism of the PPARgamma gene; a polymorphism in a gene encoding Tryptophan 2, 3-Dioxygenase (TDO2); a polymorphism in a gene encoding TCP-I; a polymorphism in a gene encoding Mc4R; a polymorphism in a gene encoding CART; a polymorphism in a gene encoding interleukin-1 beta; a polymorphism in a gene encoding tumor necrosis factor-alpha; a polymorphism in a gene encoding an intracellular adhesion molecule; a polymorphism in a gene encoding interleukin-8, a polymorphism in a gene encoding and interleukin-10; a polymorphism in a gene encoding interferon-alpha; a polymorphism in a gene encoding Ras-Protein and (HLA-DRB1 0404 and OlOlor PTPN22 R620W); the Dopamine Receptor D3 Ser9Gly (−205-G/A, −7685-G/C) polymorphism; a polymorphism in a gene encoding Glutamine: fructose-6-phosphate amidotransferase (GFPT1 or GFPT 2), optionally polymorphisms in exon 14, optionally 1471V, or 3' UTR; or a polymorphism in a gene encoding glucosamine 6-P acyltransferase; a polymorphism in Aggrecan proteoglycan allele 27; a polymorphism in a gene encoding 11-beta hydroxysteroid dehydrogenase type 1; a polymorphism in a gene encoding FK506 binding protein 5; a polymorphism in a gene encoding serum/glucosteroid kinase; a polymorphism in a gene encoding tryptophan 2,3 dioxygenase; a polymorphism in a gene encoding Myelin; a polymorphism in a gene encoding a Myelin associated glycoprotein, optionally myelin oligodendrocyte glycoprotein (MOG), optionally a polymorphism in a tetranucleotide TAAA repeat (M0G4), C10991T SNP; a polymorphism in a gene encoding Edg2; a polymorphism in a gene encoding Fgfr2; a polymorphism in a gene encoding Decorin; a polymorphism in a gene encoding Brevican; a polymorphism in a gene encoding Neurotensin (NT) receptors-1; a polymorphism in a gene encoding Neurotensin (NT) receptor-2; a polymorphism in a gene encoding Neurotensin (NT) receptor-3; a polymorphism in a gene encoding Proenkephalin; a polymorphism in a gene encoding prodynorphin, optionally 946C>G; a polymorphism in a gene encoding Bdnf (Neurotrophic Factor, optionally BDNF Val66Met and −281 C>A, T allele of the C270T); a polymorphism in a gene encoding Sgk (Serum- and glucose-regulated kinase (SGK 1), optionally SNP Intron 6, Exon 8 (CC, CT, TT); a polymorphism in a gene encoding Gabl; Id2; a polymorphism in a gene encoding COMT; a polymorphism in a gene encoding ANKK1; a polymorphism in a gene encoding DAT1; a polymorphism in a gene encoding DBH; a polymorphism in a gene encoding HTT; a polymorphism in a gene encoding HTR1A; a polymorphism in a gene encoding HTR1D; a polymorphism in a gene encoding HTR2A; a polymorphism in a gene encoding HTR2C, optionally 5-HT-2A, 5-HT 2B, 5-HT-4, and 5-HT-7); a polymorphism in a gene encoding ADRA2A; a polymorphism in a gene encoding ADRA2; a polymorphism in a gene encoding NET; a polymorphism in a gene encoding MAOA; a polymorphism in a gene encoding GABRA3; a polymorphism in a gene encoding GABRB3; a polymorphism in a gene encoding CNR1; a polymorphism in a gene encoding CNRA4; a polymorphism in a gene encoding NMDAR1; a polymorphism in a gene encoding POMC; a polymorphism in a gene encoding MGPAT; a polymorphism in a gene encoding NYP; a polymorphism in a gene encoding AgRP; a polymorphism in a gene encoding OBR; a polymorphism in a gene encoding Mc3R:UCP-1; a polymorphism in a gene encoding GLUT4; a polymorphism in a gene encoding PDGS; a polymorphism in a gene encoding ALdB; a polymorphism in a gene encoding LNC2; a polymorphism in a gene encoding E23K Kir6.2; a polymorphism in a gene encoding steroid sulfatase (STS); a polymorphism G82G in PTPN1; the IVS6+G82A polymorphism; a polymorphism in a gene encoding Sulfonylurea receptor 1; a polymorphism in a gene encoding beta(3)-AR Trp64Arg; a polymorphism in a gene encoding PC1; a polymorphism in a GHRELIN gene; a polymorphism in a gene encoding FKBP5; a polymorphism in a gene encoding a VITAMIN D RECEPTOR, optionally BSMI AND FOKI; a polymorphism in a gene encoding lymphoid tyrosine phosphatase (LYP), optionally a polymorphism in a gene encoding protein tyrosine phosphatase-22 (PTPN22) gene, and a polymorphism in a gene encoding any sodium ATPAse.

Allelic analysis includes identifying at least one mutation that is a polymorphism selected from the group consisting of a polymorphism (Rs value of SNP) of a gene encoding DRD2 (Rsl800497, Rs6278, Rs6276, RslO79594, Rs 6275, Rsl801028, Rsl076560, Rs2283265, RslO79727, RslO76562, Rsll25394, Rs4648318, Rs4274224, Rs7131056, Rs4648317, Rsl799732, Rsl799978; 5HT2A (Rs6314, Rs3742278, Rs6561333, Rsl923886, Rs643627, Rs2770292, Rsl928040, Rs2770304, Rs594242, Rs6313; ANKK1 (RS2734849, RS1800497, Rsll604671, Rs4938016); OPRK1(Rs35160174, Rs35373196, Rs34709943 RS6473797) OPRMI (Rs510769, Rs553202, Rs514980, Rs561720, Rs534673, Rs524731, Rs3823010, Rs3778148, Rs7773995, RS495491, Rsl2333298, Rsl461773, Rsl381376, Rs3778151, Rs506247, Rs563649, Rs9479757, Rs2075572, Rsl0485057, Rs540825, Rs562859, Rs548646, Rs648007, Rs9322447, Rs681243, Rs609148, Rs3798687, Rs648893); COMT (Rs737864, Rs933271, Rs5993882, Rs740603, MTRs4646312, Rsl65722, Rs6269, Rsl7699); SLC6A3 (Rsl2516948, Rsl042098, Rs40184, Rsll564773, Rslll33767, Rs6876225, Rs3776512, Rs2270912, Rs6347, Rs27048, Rs37022, Rs2042449, Rs464069, Rs463379, Rs403636, Rs2617605, Rsl3189021, Rs6350, Rs2975223, Rs2963238, Rs 11564752 Rs2975226); HTR3B(Rs3758987, Rs2276307, Rs3782025, Rsl672717); NOS3 (Rs891512, Rsl808593, Rs2070744, Rs3918226, Rs7830); PPARG (Rsl801282, Rs2938392, Rsll75542, Rsl7036314, Rsl805192, Rs4684847, Rs2938392, Rs709157, Rs709158, Rsll75542); ChREBP (Rs3812316); FTO (Rs8050136, Rsl421084, Rs9939609, Rsl861868, Rs9937053, Rs9939973, Rs9940128, Rsl558902, RslO852521, Rsl477196, Rsll21980, Rs7193144, Rsl6945088, Rs8043757, Rs3751812, Rs9923233, Rs9926289, Rsl2597786, Rs7185735, Rs9931164, Rs9941349, Rs7199182, Rs9931494, Rsl7817964, Rs7190492, Rs9930506, Rs9932754, Rs9922609, Rs7204609, Rs8044769, Rsl2149832, Rs6499646, Rsl421090, Rs2302673); TNFalpha (Rsl799964, Rsl800629, Rs361525, Rsl800610, Rs3093662); MANEA (Rsll33503); LeptinOb (Rs4728096, Rsl2536535, Rs2167270, Rs2278815, Rsl0244329, Rsll763517, Rsll760956, RslO954173); PEMT (Rs4244593, Rs936108); MAO-A (Rs3788862, Rsl465108, Rs909525, Rs2283724, Rsl2843268, Rsl800659, Rs6323, Rsl799835, Rs3027400, Rs979606, Rs979605 Rsll37070); CRH (Rs7209436, Rs4792887, Rsll0402, Rs242924, Rs242941, Rs242940, Rs242939, Rs242938, Rsl73365, Rsl876831, Rsl876828, Rs937, Rs878886 Rs242948); ADIPOQ (Rsl7300539, Rs2241766); STS (Rsl2861247); VDR (Rsl7467825, Rs731236, Rsl544410, Rs2229828, Rs2228570, Rs2238136); DBI (Rs3091405, Rs3769664, Rs3769662, Rs956309, Rs8192506); GABRA6 (Rs3811995, Rs3219151, Rs6883829, Rs3811991); GABRB3 (Rs2912582, Rs2081648, Rsl426217, Rs754185, Rs890317, Rs981778, Rs2059574); MTHFR(Rs4846048, Rsl801131, Rsl801133, Rs2066470); MLXIPL[carbohydrate binding element] (Rs3812316, Rsl7145738); VEGF (Rs2010963, Rs833068, Rs3025000, Rs3025010, Rs3025039, Rs3025053); DRD4 (Rs936460, Rs41298422, Rs3758653, Rs936461, Rsl2720373, Rs747302, Rsl800955, Rs916455, Rs916457, Rs7 124601); CLOCK (Rsl801260, Rs934945, Rsl3033501); Melatonin (any polymorphism); Orexin (all polymorphisms), PENK (RS16920581, RS1437277, RS1975285, RS260998, RS2609997), and CB1 (RS1049353).

The question is which of all these genes will result in predicting clinical outcome. This challenge was overcome by the methodology of the present invention.

Utility of the Present Invention

The genetic addictive risk analysis methods and kits disclosed and taught herein have many industrial benefits for the entire RDS field.

For instance, these will reduce/eliminate guessing related to administration of potent opioids to treat both acute and chronic pain. By implementing the genetic addictive risk analysis test, which has now shown to predict clinical severity (alcohol as an example) for addiction, will be seen as a tremendous breakthrough in the addiction field. In fact a focus group conducted with Dominion Diagnostics (the developer of the genetic test) revealed 100% excitement for its utilization in the addiction industrial space.

One of the major issues in addiction treatment is quilt and denial of the pathological hypodopaminergic trait/state. With information provided by genetic addictive risk analysis, the patient/individual will be able to grasp and understand their risk just as if one was determining risk for other chronic diseases like diabetes.

Other benefits include, but are not limited to, determination of medical monitoring (treatment medication) as a function of different reward gene polymorphisms.

In addition, the development of personalized medicine has already been shown by targeting reward gene polymorphisms utilizing a variation of genetic addictive risk analysis for obesity. There is indeed a great need for the commercialization of a predictive genetic based test and an individual risk for all addictive behaviors as espoused in the RDS framework.

Utilization of the genetic addictive risk analysis test in clinical practice should: (1) reduce denial; (2) reduce guilt; (3) reduce erroneous-prediction of relapse chance; (4) lead to appropriate therapeutic targets based on known gene polymorphisms and medication dosing; (5) improve drug selection and evaluation; (6) analyze patient risk for pain medication tolerance, dependence, and/or abuse; and (7) improve outcomes based on medical necessity.

It has been shown that significant association of genetic risk stratification as a predictor of ASI testing. To Applicant's knowledge this is the only set of gene and respective alleles provide patient based information to assist the clinician with an objective biologically based diagnostic tool to support a novel treatment plan.

While embodiments of the invention have been shown and described, modifications thereof can be made by one skilled in the art without departing from the spirit and teachings of the invention. The embodiments described and the examples provided herein are exemplary only, and are not intended to be limiting. Many variations and modifications of the invention disclosed herein are possible and are within the scope of the invention. Accordingly, other embodiments are within the scope of the following claims. The scope of protection is not limited by the description set out above, but is only limited by the claims which follow, that scope including all equivalents of the subject matter of the claims.

The disclosures of all patents, patent applications, and publications cited herein are hereby incorporated herein by reference in their entirety, to the extent that they provide exemplary, procedural, or other details supplementary to those set forth herein.

REFERENCES

H. C. Anchordoquy et al., "Genotyping of three candidate genes after whole-genome preamplification of DNA collected from buccal cells," *Behav Genet.* 2003, 33(1):73-8 ("Anchordoquy 2003").

K. Blum et al., "Buprenorphine Response as a Function of Neurogenetic Polymorphic Antecedents: Can Dopamine Genes Affect Clinical Outcomes in Reward Deficiency Syndrome (RDS)"*J Addict Res Ther.*, 2014, 5 pii: 1000 ("Blum 2014").

K. Blum et al., *Molecular Neurobiology of Addition Recovery: The* 12 *Steps Program and Fellowship*, Springer Science & Business Media (2013) ("Blum 2013").

K. Blum et al., "Generational association studies of dopaminergic genes in reward deficiency syndrome (RDS) subjects: selecting appropriate phenotypes for reward dependence behaviors," *Int J. Environ Public Health*, 2011, 8(12):4425-59 ("Blum 2011").

K. Blum et al., "Reward deficiency syndrome: a biological model for diagnostics and treatment of impulsive, additive, and compulsive behavior," *J. Psychoactive Drugs*, 2000, 32 Suppl:1-iv, 1-112 ("Blum 2000").

K. Blum et al., "The D2 dopamine receptor gene as a determinant of reward deficiency syndrome," *J R Soc. Med*, 1996, 89(7):396-400 ("Blum 1996").

K. Blum K. et al., "Allelic association of human dopamine D2 receptor gene in alcoholism," *JAMA*, 1990, 263(15), 2055-2060 ("Blum 1990").

A. Bowirrat et al., "Relationship Between Dopaminergic Neurotransmission, Alcoholism, and Reward Deficiency Syndrome," *American Journal of Medical Genetics Part B (Neuropsychiatric Genetics)*, 2005 132B:29-37 ("Bowirrat 2005").

G. Di Chiara et al., "Drugs abused by humans preferentially increase synaptic dopamine concentrations in the mesolimbic system of freely moving rats," *Proc Natl Acad Sci USA*, 1988, 85:5274-5278 ("Di Chiara 1988").

D. E. Comings et al., "Reward deficiency syndrome: genetic aspects of behavioral disorders," *Prog Brain Res*, 2000, 126:325-41 ("Comings 2000").

C. Dackis et al., "Neurotransmitter and neuroendocrine abnormalities associated with cocaine use," *Psychiatr Med.*, 1985, 3(4):461-483 ("Dackis 1985").

R. H. Don et al., "'Touchdown' PCR to circumvent spurious priming during gene amplification," *Nucleic Acids Res.*, 1991, 19(14):4008 ("Don 1992").

D. T. Eisenberg et al., "Season of birth and dopamine receptor gene associations with impulsivity, sensation seeking and reproductive behaviors," *PLoS One*, 2007, 2:e1216 ("Eisenberg 2007").

Jamie Feusner et al., "GABAA receptor β3 subunit gene and psychiatric morbidity in a post-traumatic stress disorder population," *Psych. Res Volume* 2001, 104(2): 109-117.

B. C Haberstick, et al., "Simple Sequence Repeats In The National Logitudinal Study Of Adolescent Health: An Ethically Diverse Resource For Genetic Analysis Of Health Behavior," *Behav Genet.*, 2014, 44(5): 487-497 ("Haberstick 2014").

B. C Haberstick, et al., "Genotyping of three single nucleotide polymorphisms following whole genome preamplification of DNA collected from buccal cells," *Behav Genet.*, 2004, 34:541-547 ("Haberstick 2004").

J. Hietala et al., "Striatal D2 dopamine receptor binding characteristics in vivo in patients with alcohol dependence," *Psychopharmacology (Berl)*, 1994, 116:285-290 ("Hietala I 1994").

J. Hietala J et al., "Striatal D2 dopamine receptor characteristics in neuroleptic-naive schizophrenic patients studied with positron emission tomography," *Arch Gen Psychiatry*, 1994, 51:116-123 ("Hietala II 1994").

X. Hu et al., "An expanded evaluation of the relationship of four alleles to the level of response to alcohol and the alcoholism risk," *Alcohol Clin Exp Res.* 2005, 29(1):8-16 ("Hu 2005").

K. A. Johnson et al., "Absence of the 7-Repeat Variant of the DRD4 VNTR Is Associated With Drifting Sustained Attention in Children With ADHD But Not In Controls," *American Journal of Medical Genetics Part B (Neuropsychiatric Genetics*, 2008, 147B:927-937 ("Johnson 2008").

J. Kircheiner et al., "A 40-basepair VNTR polymorphism in the dopamine transporter (DAT1) gene and the rapid response to antidepressant treatment," *The Pharmacogenomics Jounral*, 2007, 7:48-55 ("Kircheiner 2007").

K. J. Livak, "Allelic discrimination using fluorogenic probes and the 5' nuclease assay. Genetic Analysis," *Biomol Eng*, 1999, 14:143-149 ("Livak 1999").

M. Melis et al., "The dopamine hypothesis of drug addiction: hypodopaminergic state," *Int Rev Neurobiol*, 2005, 63:101-154 ("Melis 2005").

E. P. Noble, et al., "D2 dopamine receptor gene in psychiatric and neurologic disorders and its phenotypes," *Am J Med Genet B Neuropsychiatr Genet*, 2003, 116B(1):103-25 ("Noble 2003").

R. Picetti et al., "Addiction and stress clues for cocaine pharmacotherapies," *Current Pharmaceutical Designs*, 2013, 18(40), 7065-7080 ("Picetti 2013").

R. B. Rothman et al., "Dual dopamine/serotonin releasers as potential medications for stimulante and alcohol addictions," *AAPS J*, 2007, 9(1):E1-E10 ("Rothman 2007").

N. D. Volkow et al., "Role of dopamine, the frontal cortex and memory circuits in drug addiction: insight from imaging studies," *Neurobiol Lern Mem*, 2002, 78:610-24 ("Volkow 2002").

N. D. Volkow, et al., "Low level of brain dopamine D2 receptors in methamphetamine abusers: association with metabolism in the orbitofrontal cortex, *Am J Psychiatry*, 2001, 158:2015-2021 ("Volkow 2001").

J. R. Wendland et al., "Simultaneous genotyping of four functional loci of human SLC6A4, with a reappraisal of 5HTTLPR and rs25531," *Mol Psychiatr.*, 2006, 11:224-226 ("Wendland 2006").

What is claimed is:

1. A method of obtaining and utilizing a risk score for evaluating stratification of a plurality of ranges for a genetic addiction risk comprising the steps of:
   (a) obtaining a biological sample from a subject;
   (b) performing an allelic analysis on the biological sample to detect the presence of a plurality of pre-determined alleles in the biological sample, wherein
      (i) each of the alleles in the plurality of pre-determined alleles is associated with a gene in a plurality of pre-determined genes,
      (ii) there are at least ten genes in the plurality of pre-determined genes,
      (iii) there is at least one allele for each of the genes in the plurality of pre-determined genes, and
      (iv) the plurality of pre-determined alleles comprise
         (A) allele G of gene DRD1;
         (B) allele A1 of gene DRD2;
         (C) allele C of gene DRD3;
         (D) allele C of gene DRD4;
         (E) allele 9R of gene DAT1;
         (F) allele 7-11R of gene DRD4;
         (G) allele S or L of gene HTTLPR;
         (H) allele 4R of gene MAOA;
         (I) allele G of gene COMT;
         (J) allele G of gene OPRM1; and
         (K) allele 181 of gene GABRB3;
   (c) assigning a count for each of the alleles in the plurality of pre-determined alleles that was detected to be present in the biological sample, wherein the count for a particular allele is the number of the particular allele detected to be present in the biological sample;
   (d) determining a risk score for the subject based upon the count, wherein
      (i) the risk score is the sum of the counts,
      (ii) stratification of the plurality of ranges of the risk score identifies a severity of the genetic addiction risk of a reward deficiency syndrome behavior,
      (iii) the risk score in a first pre-determined range for the reward deficiency syndrome behavior identifies a low genetic addiction risk for the subject, and
      (iv) the risk score in a second pre-determined range for the reward deficiency syndrome behavior identifies a high genetic addiction risk; and
   (e) administering treatment based upon the severity of the genetic addition risk identified for the subject, wherein, for a high addictive risk identified subject, the treatment comprises treating the subject for the reward deficiency syndrome behavior and further comprises entry of the subject in a residential treatment program for the reward deficiency syndrome behavior of the subject and medically monitoring the reward deficiency syndrome behavior of the subject.

2. The method of claim 1, wherein the plurality of pre-determined alleles consists of:
(a) allele G of gene DRD1;
(b) allele A1 of gene DRD2;
(c) allele C of gene DRD3;
(d) allele C of gene DRD4;
(e) allele 9R of gene DAT1;
(f) allele 7-11R of gene DRD4;
(g) allele S or L of gene HTTLPR;
(h) allele 4R of gene MAOA;
(i) allele G of gene COMT;
(j) allele G of gene OPRM1; and
(k) allele 181 of gene GABRB3.

3. The method of claim 1, wherein (ii) the risk score in a third range for the reward deficiency syndrome behavior identifies a moderate genetic addictive risk.

4. The method of claim 1, wherein
(i) the genetic addictive risk behavior is for drugs, and
(ii) the second pre-determined range is 4 and above.

5. The method of claim 4, wherein the first predetermined range is from 0 to 1.

6. The method of claim 1, wherein
(i) the genetic addictive risk behavior is for alcohol, and
(ii) the second pre-determined range is 8 and above.

7. The method of claim 6, wherein the first predetermined range is from 0 to 3.

8. The method of claim 1, wherein the reward deficiency syndrome behavior is selected from the group consisting of addictive behaviors, impulse behaviors, obsessive compulsive behaviors, personality disorder behaviors, and combinations thereof.

9. The method of claim 3, wherein
(i) the genetic addictive risk behavior is for drugs,
(ii) the first pre-determined range is from 0 to 1,
(iii) the second pre-determined range is 4 and above, and
(iv) the third pre-determined range is from 2 to 3.

10. The method of claim 3, wherein
(i) the genetic addictive risk behavior is for alcohol,
(ii) the first pre-determined range is from 0 to 3,
(iii) the second pre-determined range is 8 and above, and
(iv) the third pre-determined range is from 4 to 7.

11. The method of claim 1, wherein
(i) the genetic addictive risk behavior is chemical dependency, and
(ii) for a high addictive risk identified subject, the treatment further comprises providing support to reduce the chance of relapse by the diagnosed subject.

12. The method of claim 11, wherein the second pre-determined range is 4 and above.

13. The method of claim 11, wherein, the count for the allele A1 of gene DRD2 is at least one.

14. A method of obtaining and utilizing a risk score for evaluating stratification of a plurality of ranges for a genetic addiction risk comprising the steps of:
(a) obtaining a biological sample from a subject;
(b) performing an allelic analysis on the biological sample to detect the presence of a plurality of pre-determined alleles in the biological sample, wherein
(i) each of the alleles in the plurality of pre-determined alleles is associated with a gene in a plurality of pre-determined genes,
(ii) there are at least ten genes in the plurality of pre-determined genes,
(iii) there is at least one allele for each of the genes in the plurality of pre-determined genes, and
(iv) the plurality of pre-determined alleles comprise
(A) allele G of gene DRD1;
(B) allele A1 of gene DRD2;
(C) allele C of gene DRD3;
(D) allele C of gene DRD4;
(E) allele 9R of gene DAT1;
(F) allele 7-11R of gene DRD4;
(G) allele S or L of gene HTTLPR;
(H) allele 4R of gene MAOA;
(I) allele G of gene COMT;
(J) allele G of gene OPRM1; and
(K) allele 181 of gene GABRB3;
(c) assigning a count for each of the alleles in the plurality of pre-determined alleles that was detected to be present in the biological sample, wherein the count for a particular allele is the number of the particular allele detected to be present in the biological sample;
(d) determining a risk score for the subject based upon the count, wherein
(i) the risk score is the sum of the counts,
(ii) stratification of the plurality of ranges of the risk score identifies a severity of the genetic addition risk of a reward deficiency syndrome behavior, wherein the reward deficiency syndrome behavior is opioid dependency,
(iii) the risk score in a first pre-determined range for the reward deficiency syndrome behavior identifies a low genetic additive risk for the subject, and
(iv) the risk score in a second pre-determined range for the reward deficiency syndrome behavior identifies a high genetic additive risk; and
(e) administering treatment based upon the severity of the genetic addition risk identified for the subject, wherein, for a high addictive risk identified subject, the treatment comprises providing pain treatment in which the use of opioids is avoided.

15. The method of claim 14, wherein the pain treatment comprises the use of non-steroidal anti-inflammatory drugs.

16. The method of claim 14, wherein the second pre-determined range is 4 and above.

17. A method of obtaining and utilizing a risk score for evaluating stratification of a plurality of ranges for a genetic addiction risk comprising the steps of:
(a) obtaining a biological sample from a subject;
(b) performing an allelic analysis on the biological sample to detect the presence of a plurality of pre-determined alleles in the biological sample, wherein
(i) each of the alleles in the plurality of pre-determined alleles is associated with a gene in a plurality of pre-determined genes,
(ii) there are at least ten genes in the plurality of pre-determined genes,
(iii) there is at least one allele for each of the genes in the plurality of pre-determined genes, and
(iv) the plurality of pre-determined alleles comprise
(A) allele G of gene DRD1;
(B) allele A1 of gene DRD2;
(C) allele C of gene DRD3;
(D) allele C of gene DRD4;
(E) allele 9R of gene DAT1;
(F) allele 7-11R of gene DRD4;
(G) allele S or L of gene HTTLPR;
(H) allele 4R of gene MAOA;
(I) allele G of gene COMT;
(J) allele G of gene OPRM1; and
(K) allele 181 of gene GABRB3;

(c) assigning a count for each of the alleles in the plurality of pre-determined alleles that was detected to be present in the biological sample, wherein the count for a particular allele is the number of the particular allele detected to be present in the biological sample (d) determining a risk score for the subject based upon the count, wherein
  (i) the risk score is the sum of the counts,
  (ii) stratification of the plurality of ranges of the risk score identifies a severity of the genetic addition risk of a reward deficiency syndrome behavior,
  (iii) the risk score in a first pre-determined range for the reward deficiency syndrome behavior identifies a low genetic additive risk for the subject, and
  (iv) the risk score in a second pre-determined range for the reward deficiency syndrome behavior identifies a high genetic additive risk; and (e) administering treatment based upon the severity of the genetic addition risk identified for the subject, wherein, for a high addictive risk identified subject, the treatment comprises providing a dopamine regulator.

18. The method of claim 17, wherein the second pre-determined range is 4 and above.

19. The method of claim 18, wherein, the count for the allele A1 of gene DRD2 is at least one.

20. The method of claim 17, wherein, the count for the allele G of gene OPRM1 is at least one.

21. The method of claim 14, wherein the plurality of pre-determined alleles consists of:
  (a) allele G of gene DRD1;
  (b) allele A1 of gene DRD2;
  (c) allele C of gene DRD3;
  (d) allele C of gene DRD4;
  (e) allele 9R of gene DAT1;
  (f) allele 7-11R of gene DRD4;
  (g) allele S or L of gene HTTLPR;
  (h) allele 4R of gene MAOA;
  (i) allele G of gene COMT;
  (j) allele G of gene OPRM1; and
  (k) allele 181 of gene GABRB3.

22. The method of claim 17, wherein the plurality of pre-determined alleles consists of:
  (a) allele G of gene DRD1;
  (b) allele A1 of gene DRD2;
  (c) allele C of gene DRD3;
  (d) allele C of gene DRD4;
  (e) allele 9R of gene DAT1;
  (f) allele 7-11R of gene DRD4;
  (g) allele S or L of gene HTTLPR;
  (h) allele 4R of gene MAOA;
  (i) allele G of gene COMT;
  (j) allele G of gene OPRM1; and
  (k) allele 181 of gene GABRB3.

* * * * *

SEQUENCE LISTING

```
<160> NUMBER OF SEQ ID NOS: 8

<210> SEQ ID NO 1
<211> LENGTH: 30
<212> TYPE: DNA
<213> ORGANISM: Homo sapiens

<400> SEQUENCE: 1
accggcaccg gcaccagtac ccgcaccagt                                    30

<210> SEQ ID NO 2
<211> LENGTH: 2039
<212> TYPE: DNA
<213> ORGANISM: Homo sapiens
<220> FEATURE:
<221> NAME/KEY: misc_feature
<222> LOCATION: (1193)..(1193)
<223> OTHER INFORMATION: n is a, c, g, or t
```

<400> SEQUENCE: 2

```
tctcccgcct ggcgttgccg ctctgaatgc cagcacctaa ccctaatgt ccctactgca      60
gccctcccag catccccct gcaacctccc agcaactccc tgtaccctc ctaggatcgc      120
tcctgcatcc cccattatcc ccccttcac ccctcgcggc atccccctg cacccccrgc      180
atcccccctg cagccccccc agcatctccc ctgcacccc agcatccccc ctgcagccct      240
tccagcatcc ccctgcacct ctcccaggat ctccctgca accccatta tccccctgc      300
acccctcgca gtatcccccc tgcacccccc agcatccccc catgcacccc cggcatcccc      360
cctgcacccc tccagcattc tccttgcacc ctaccagtat tccccgcat ccggcctcc      420
aagcctcccg cccaccttgc ggtccccgcc ctggcgtcta ggtggcacca gaatcccgcg      480
cggactccac ccgctgggag ctgccctcgc ttgcccgtgg ttgtccagct cagtccctct      540
agacgctcag cccaaccggc cgcacagttt tcaggggtca gttcctccaa gtacaagggg      600
cggtggcttc tctggagctg caaacttgtc actgctattt cctttcggtc ttctacttcc      660
tatcgttcct ggcctcctct tggggagagg tagagccctc tccttccgc ctcagggaca      720
acccaaagca agtactgcat gtgcccttt taaagtttta aataattta gcaaaaagga      780
tattaacatt aaatcaattt ttaaacttt tgaaaaatt atcaaaacta catgcacatg      840
gttcaaaaca ataggctcct gctgggccct ttcagataat tcaaattgtc accaggttgg      900
agtgcagtgg ttcgatcacg gctcactgca gcctcgactc ccgggctcag ctgatcctcc      960
acctcagcct cctgagtagc tgggaacaca agcgcgagca accacgcccg gctaattaaa     1020
aaaatttttt ttctagagat ggggtcttgc tgtgttgccc aggctggtct tgaattcctg     1080
ggctcaagca atcctcccgc ctcagcctcc caaagcactg tgctccttt tgacgcagct     1140
ttgaactgta gctggttaac aaaatgagaa ccagttcttc attccttcat tgnggaagtc     1200
tttattgtga gactctgggg acggagagga attagacaag ggcctctaag ctgagctcac     1260
atcccagccg gtcagtcaga taaacgcatg ggtatcgagt actgctaggt cccaggaaga     1320
aagagagagc agctttcggg atggggacga tggggaggtg tccgaggtca agagaaagcg     1380
gcacgagcag acccctgtgt gccgtcctgt gggcgcgggg cggcagggga ggcgcacacc     1440
tgctcctttg tgcagcctcc cccctcccgc aaagttaaag agcaggaaag tcaggattcc     1500
tcgctcggcc ctgccctgcc ggctgctccg cgctccgctc ctccctgcga gcgtgtgtgt     1560
gtgtcggggg tccctcccct cctggctctg gggtcgggcg cgcacccgc cccgtagcgc     1620
ggcccctccc tggcgagcgc aaccccatcc agcgggagcg cggagccgcg gccgcggggga     1680
agcattaagt ttattcgcct caaagtgacg caaaaattct tcaagagctc tttggcggcg     1740
gctatctaga gatcagacca tgtgagggcc gcgggtaca aatacggccg cgccggcgcc     1800
cctccgcaca gccagcgccg ccgggtgcct cgagggcgcg aggccagccc gcctgcccag     1860
cccgggacca gcctccscgc gcagcctggc aggtgggtcc gcttttcctc tccgcctcga     1920
acccacgttt cttttccagac cttcttcccc gcctcgggga ggggggataga accgctgcgc     1980
cccaccgccc tgcgaggagg cgaggaggtg catgcgcccc agcggtgggc gccggatcc     2039
```

<210> SEQ ID NO 3
<211> LENGTH: 1001
<212> TYPE: DNA
<213> ORGANISM: Homo sapiens

<400> SEQUENCE: 3

| | |
|---|---:|
| agacaaggtc catgccacac tgatcaggat gaaggctgcc ttgggggtca tctttctctc | 60 |
| ataccggaaa gggctggaga tagcccaata cctgtccacg ctgatcacac agaggttgag | 120 |
| gatggatgca gtggagcaca tgatgtcaaa ggccacccag atgttacaga aggacccaaa | 180 |
| gggccagaag ccagcaatct cagccactgc cttccagggc atgaccagga cggccaccaa | 240 |
| gagatctgac acagccaagg agatgacaaa gaagttggtc accttggacc gcaggtgtcg | 300 |
| gaacctgata acggcagcac agaccagcgt gttccccagg agcgtggaca ggatgagcag | 360 |
| cgacaggaaa caggcagtga ggatacgaac agagaagtcc ctctccacca ccagcccagt | 420 |
| cccgtccatg gcagaggtgt tcagagtcct catcttccta agagaaagca catcaggggc | 480 |
| tctgacaccc ctcaagttcc yaagcaggga ataggggtca gtcagatttc caggagtcct | 540 |
| ccccaccagg cagcactttg cacagccaga ttgcttccct ggcagagggc ctcaccaaca | 600 |
| ttccatgaga ggaccgcttg agtggcaatc caagtcaatc ccgtggatgg tcactcttga | 660 |
| tttctacatc tgtcttctga ctcccttgct gcaggtcact gtcttgggca ccagaaagcc | 720 |
| cctgaattcc ccaaataaag cactggcttt ttagcatatt ctaaatcatc aatccagtga | 780 |
| ctcctgggcc tctgctctgc tagtcagttg caatcacatt tcggggctgt tgcttttctg | 840 |
| gtggtgacag gagattctcc ccttctgaga ctcagctgaa aatacatgtc ttctcgctcc | 900 |
| tccaagcccc tggctcctca gcagctctcc aaacgcctta aaaagcaaaa ggaaaacaca | 960 |
| cggtctttct ccaagactta agcagatggc atcattactc a | 1001 |

<210> SEQ ID NO 4
<211> LENGTH: 1001
<212> TYPE: DNA
<213> ORGANISM: Homo sapiens

<400> SEQUENCE: 4

| | |
|---|---:|
| tccaggcgag aggccccaag tagtctaaat ttctttcttt ctttcttttt tatatggagt | 60 |
| ctcgctctgt tgcccaggct ggagtgcagt ggtgcgatct cggctcactg caacctctgc | 120 |
| ctcctgggtt caaggaattc tcctgcctca gcctcctgg tagttgggat tacaggcacg | 180 |
| tgccaccata cccagctaaa ttttgtattt ttagcagaga caggggttttg ccatgttggc | 240 |
| caggctggcc tcaaactctt gatatcaggt gatctgcctg cctcagcctc ccaaagtgct | 300 |
| gggattacag acgtgagcca ccacggctgg ccaagttgtc taaatttcca tctcggctcc | 360 |
| tggcttagaa ccacccagag tggccactga cggctccttg ccctctagga aggacatgat | 420 |
| gccctgcttt cggctgcgga gggccagttg caggggtgtg cagctcactc catcctggac | 480 |
| gtccagctgg gcgcctgcct ygaccagcac tttgaggatg gctgtgttgc ccttgagggc | 540 |
| ggccaggtgg gcgggtgtcc agcccacctt gttgcgggcg tggacatttg cgtgatgttc | 600 |
| taggaggttg atgacactca ggaaggtgct cctctggacc gccaggtgga ggggtgtcca | 660 |
| gcctgactgc tctgcagcat tggggtcagc cccacactgc agcagtgctg acaccaccgc | 720 |
| ctcctccccg tggcgtgcag ctaggtgcag gggagtccag ttcacagctc caagagcacc | 780 |
| catgtttgcg tggctctctg ccagcagatg gatgatctcc aggtggccct tgtaggctgc | 840 |
| tagatgcagg ggtgtccagc cctggtgggt gggcagctca aggctggctc cgtacctgag | 900 |
| cagcatcttg cagatcaggt atttgcccct ggcagctgca gtgtgcagtg ggccgtagcc | 960 |
| gctctggtca agggcatcag ggaccgctcc actcttcagc a | 1001 |

<210> SEQ ID NO 5
<211> LENGTH: 2203

<212> TYPE: DNA
<213> ORGANISM: Homo sapiens

<400> SEQUENCE: 5

```
gtctgccaca gccaggctca ctactaagta gttggtggta gtctgcaggg cccgctcctt      60
cagcacagcc atgcacacca ggccattgcc gaagacgatg ccaggatga gcgcgcagta      120
ggagagggca tagtaggcat gtgggcgggc ctggctggca cctgtggagt tctctgcccc    180
acaggtgtag ttcaggtggc yactcagctg gctcagagat gccatagccc agagggaggt    240
gcgtgatgcc aagggcttc ctgtgaggag acagaaaaca atattaataa aatcagactc     300
tttgggctt ggttgcttag ttacattttt ttatttattg catcagcaaa tatttattga    360
gcattttcta tatagtaggc actgttgtga gagttggaga tagagcaatg aacaaaacag    420
ataaaatctt aattccttcc ctttgaagct cccattctag aggagaagac agataataaa    480
caagataaat aaaagatgtg gtgtgttcaa taatgatacg tatattggag acaaatcaga    540
gaggcaggta agtaacgggt gaagattgtg cgtatgtgag tgagtatctg agtataatca    600
ggaactcctc atggagaaat cagcaattga gtcttgacct ggaggagatc aggaagcaga    660
ccatgcagtt atcagatgtg atagcagtct gagcagtgag aacaacacgg gccagcagga    720
agggctagca catagaagtc ataggaggga gtctggtgag gctggagcca agtgaggcag    780
gagtagaata ggagggtgtg aggtagacag attgtgcagg gctattgaaa gtaccatgct    840
tggactctga gtgagatggg aagctgttgc aggattacaa tcccagctct gctgcttcct    900
aactctggga cctttatgcat attactttac ctctctgagc tccagattct tcccatgtaa    960
aatgtgggaa taatgaaacc catctatctt agtccatttt gggttgctat aacagaacac   1020
ctgagtctgg gtaatttata aagagcagaa atttgttgtc tcacagttct gaaggctagg   1080
ggaagacata aggcctgtga cttagggagt aaccctgaaa cccaagcaaa agtgactctt   1140
gccccaagct ctagaggagg tgctatagag gagtccactc tggtcttctg ctgtggtctc   1200
ggtgttttgtg tctccctaaa ttcatatgta gaaatcctaa ttcccaatat gatggtatta   1260
ggaggtgggg gtcttttgaga ggtgattagg ttatgaggac agagccctca tgaataagat   1320
tagtgctttt ataaaagaga cccagagagc tagctaatct cttttcaccat gggaagacat   1380
agtgaaaaga cagccatcta tgaaccagaa agcaggccct caccagacac tgaatcttct   1440
ggtgccttga tcttggactt cccagccttc agaactgtca aaaatagata tctgttgttt   1500
ataaactact cagtttatgg tattttgtga tagcagccca aaaggactaa ggcaccctct   1560
actggttatg cctctaacct ctatagaatg atgttgtaac ctcccacagt gccaaggaga   1620
aggtccacta agtttacaac cctgtctaga ccacactcag ggaattctct acccaactgc   1680
tcagagcctt tttccaagac atcacgggtc tcattctaaa tctctcactc tgacgggaga   1740
ctgtgccata aatgtgtagg gttcctgggg ccaagtggtg gctttcagtt agagctcaga   1800
caaatagatt ctatgtagcc tgaggttggg agagaagagg ccagggtccc tgaagcagat   1860
tagggggtggg ggcccagctt ctcctgtatg atcacatttt gtatggaatt ttgaaaggtc   1920
caggaatctt aaattcaaac ttggccttcc atgttgttac gaaggtgtat ttgtcaaggt   1980
gggaggatga aacattttac tcaatggctt gttggttaca actttaaaat atttaagcat   2040
ggtacatata gacctttatg ggaactctct cttcaggcct tggcaaaagt agaggctgac   2100
ttggtggcca gaatttgccc tcaagccagg tatctgtagc tctcccttga ttaggagacc   2160
ggcctaatca tggctgtcat tttgtacctc actttgaaat gtt                      2203
```

<210> SEQ ID NO 6
<211> LENGTH: 1001
<212> TYPE: DNA
<213> ORGANISM: Homo sapiens

<400> SEQUENCE: 6

```
tggggtccca cagagtggtg cccccttttta gtgtcttcta ggccccttag tgacagacta      60
cagaaaatac ctctcaggtc acaggtcacc cctctttggt gaagagtcca tagaattctc     120
tgctgcgctt tgcaagcact ttctcttctg cacgtttgga acctaccccg gcctgtcgtg     180
tctttctcct ggcctcctcg cgagccgaac ctactgtccg gtcccgggac ccctgccca      240
gggtcagagg ggcgcctacc tagctcacgg tcttgggccg gagggaatgg aggagggagc     300
ggggtcgacc gctcagctgt ccgcccagtt tcggaggcgg ccacgcgagg atcaactgtg     360
caacgggtgg ggccgcggct gaccgtggtg gtcgcggggg ctgagggcca gaggctgcgg     420
ggggggggcg gcgggatgag ctaggcgtcg gcggttgagt cgggcgcgga gtcggggca     480
ggggagcgg gcgtggaggg ygcgcacgag gtcgaggcga gtccgcgggg gaggcgggca     540
gagcctgagc tcaggtctt ctgcgtctgg cggaacgggc ctgggaggga ggttttgcca    600
gataccaggt ggactagggt gagcgcccga gggccgggac gcacgcacgg gccgggtagg    660
atggcgctgg cgtcgatgcc cgcgcgcttc agggcctggt ctggccgccc ctccatcctt    720
gtcggtttct cgggtcgcgg acccgcgcg gcgccgggcg atgctggcct gcccgtggcc    780
accacctcgc ttcattcccg tctctttggg ccgccgcatt cgtccacgtg cccgtctctc    840
cctgcgcaaa attccaagat gagcaaatac tgggctcacg gtggagcgcc gcgggggccc    900
ccctgagccg ggcgggtcg ggggcgggac cagggtccgg ccggggcgtg cccgagggga   960
gggactcccc ggcttgcgac ccggcgttgt ccgcggtgct c                      1001
```

<210> SEQ ID NO 7
<211> LENGTH: 1001
<212> TYPE: DNA
<213> ORGANISM: Homo sapiens

<400> SEQUENCE: 7

```
agagggcagc tctgtgttag gacacactgg ggccagccag gaagggtgga aaagataggg      60
accagcgtga gcatagaggc taagggacca tgggagctcc aagcgcgctc acagtgggga     120
ccaggtcctg ggggctgggg acaccaggga ggtgaaatac ccctccagcg ggtagggagg    180
gtgggcagag gagggccagc ggccaggcat ttgggagggg ctcctgctct ttggagagg     240
tgggggggccg tgcctgggga tccaagttcc cctctctcca cctgtgctca cctctcctcc    300
gtccccaacc ctgcacaggc aagatcgtgg acgccgtgat tcaggagcac cagccctccg    360
tgctgctgga gctgggggcc tactgtggct actcagctgt gcgcatggcc cgcctgctgt    420
caccaggggc gaggctcatc accatcgaga tcaaccccga ctgtccgcc atcccccagc    480
ggatggtgga tttcgctggc rtgaaggaca aggtgtgcat gctgacccg ttgtcagacc    540
tggaaaaagg gccggctgtg ggcagggagg gcatgcgcac tttgtcctcc ccaccaggtg    600
ttcacaccac gttcactgaa aacccactat caccaggccc ctcagtgctt cccagcctgg    660
ggctgaggaa agaccccccc agcagctcag tgagggtctc acagctctgg gtaaactgcc    720
aaggtggcac caggagggc agggacagag tggggccttg tcatcccaga accctaaaga    780
aaactgatga atgcttgtat gggtgtgtaa agatggcctc ctgtctgtgt gggcgtgggc    840
actgacaggc gctgttgtat aggtgtgtag ggatggcctc ctgtctgtga ggacgtgggc    900
```

-continued

```
actgacaggc gctgttccag gtcacccttg tggttggagc gtcccaggac atcatccccc    960
agctgaagaa gaagtatgat gtggacacac tggacatggt c                       1001

<210> SEQ ID NO 8
<211> LENGTH: 1001
<212> TYPE: DNA
<213> ORGANISM: Homo sapiens
<400> SEQUENCE: 8
tgtgtttgca cagaagagtg cccagtgaag agacctactc cttggatcgc tttgcgcaaa     60
atccacccct tttccctcct ccctccsttc cagcctccga atcccgcatg cccacgctc    120
ccctcctgca gcggtgcggg gcaggtgatg agcctctgtg aactactaag gtgggagggg    180
gctatacgca gaggagaatg tcagatgctc agctcggtcc cctccgcctg acgctcctct    240
ctgtctcagc caggactggt ttctgtaaga aacagcagga gctgtggcag cggcgaaagg    300
aagcggctga ggcgcttgga acccgaaaag tctcggtgct cctggctacc tcgcacagcg    360
gtgcccgccc ggccgtcagt accatggaca gcagcgctgc ccccacgaac gccagcaatt    420
gcactgatgc cttggcgtac tcaagttgct ccccagcacc cagccccggt tcctgggtca    480
acttgtccca cttagatggc racctgtccg acccatgcgg tccgaaccgc accgacctgg    540
gcgggagaga cagcctgtgc cctccgaccg gcagtccctc catgatcacg gccatcacga    600
tcatggccct ctactccatc gtgtgcgtgg tggggctctt cggaaacttc ctggtcatgt    660
atgtgattgt caggtaagga aagcgccagg gctccgagcg gagggttcag cggcttaagg    720
gggtacaaag agacacctaa ctcccaaggc tcaatgttgg gcgggaggat gaaagagggg    780
aggtaaactg gggggactct ggaggagacc acggacagtg attgttattt ctatgagaaa    840
acctactttt ctgttttttc ttcaactgat aaagaaagaa ttcaaaattt caggagcaga    900
gaagttgctt tggtaaaagc tacaaatgtc taggggtggg gggcggaggg aagctatagc    960
atagacttgg agcgcttcct tatactgagc aaagagggct c                       1001
```